(12) United States Patent
Flynn et al.

(10) Patent No.: US 11,013,935 B2
(45) Date of Patent: May 25, 2021

(54) ROTATING SHIELD BRACHYTHERAPY SYSTEM

(71) Applicant: University of Iowa Research Foundation, Iowa City, IA (US)

(72) Inventors: Ryan Flynn, Iowa City, IA (US); Hossein Dadkhah, Iowa City, IA (US); Kaustubh Patwardhan, Iowa City, IA (US); Myung Cho, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 103 days.

(21) Appl. No.: 16/092,851

(22) PCT Filed: Apr. 19, 2017

(86) PCT No.: PCT/US2017/028358
§ 371 (c)(1),
(2) Date: Oct. 11, 2018

(87) PCT Pub. No.: WO2017/184728
PCT Pub. Date: Oct. 26, 2017

(65) Prior Publication Data
US 2019/0126064 A1      May 2, 2019

Related U.S. Application Data

(60) Provisional application No. 62/324,432, filed on Apr. 19, 2016.

(51) Int. Cl.
*A61N 5/10* (2006.01)
*A61B 18/00* (2006.01)

(52) U.S. Cl.
CPC ......... *A61N 5/1007* (2013.01); *A61N 5/1027* (2013.01); *A61B 2018/00547* (2013.01);
(Continued)

(58) Field of Classification Search
CPC .... A61N 2005/1008; A61N 2005/1012; A61N 2005/1094; A61N 5/1007; A61N 5/1027; A61B 2018/00547
See application file for complete search history.

(56) References Cited

U.S. PATENT DOCUMENTS

2015/0148664 A1*  5/2015  Stolka ................... A61B 90/30
                                                               600/424
2015/0367144 A1* 12/2015  Flynn .................. A61N 5/1039
                                                                 600/7

* cited by examiner

*Primary Examiner* — Christine H Matthews
(74) *Attorney, Agent, or Firm* — Smith Gambrell & Russell LLP

(57) ABSTRACT

An apparatus and method for using rotating shield brachytherapy (RSBT). In an aspect, the RSBT system and method can be used to maintain or increase tumor dose relative to conventional techniques with a dramatic reduction in radiation dose to the urethra, rectum, and bladder in the treatment of prostate cancer through placing partially shielded radiation sources away from sensitive tissues. In an aspect, the invention is an apparatus and method for the precise angular and linear positioning of multiple partially-shielded radiation sources in interstitial needles. In a further aspect, the invention comprises a monitoring and control apparatus for the precise and simultaneous angular positioning of multiple shield-containing catheters in the RBST system by measuring and correcting deviations between actual and desired catheter angular positions and depth in real time before and during treatment delivery.

10 Claims, 28 Drawing Sheets
(3 of 28 Drawing Sheet(s) Filed in Color)

(52) U.S. Cl.
CPC ............... *A61N 2005/1008* (2013.01); *A61N 2005/1012* (2013.01); *A61N 2005/1094* (2013.01)

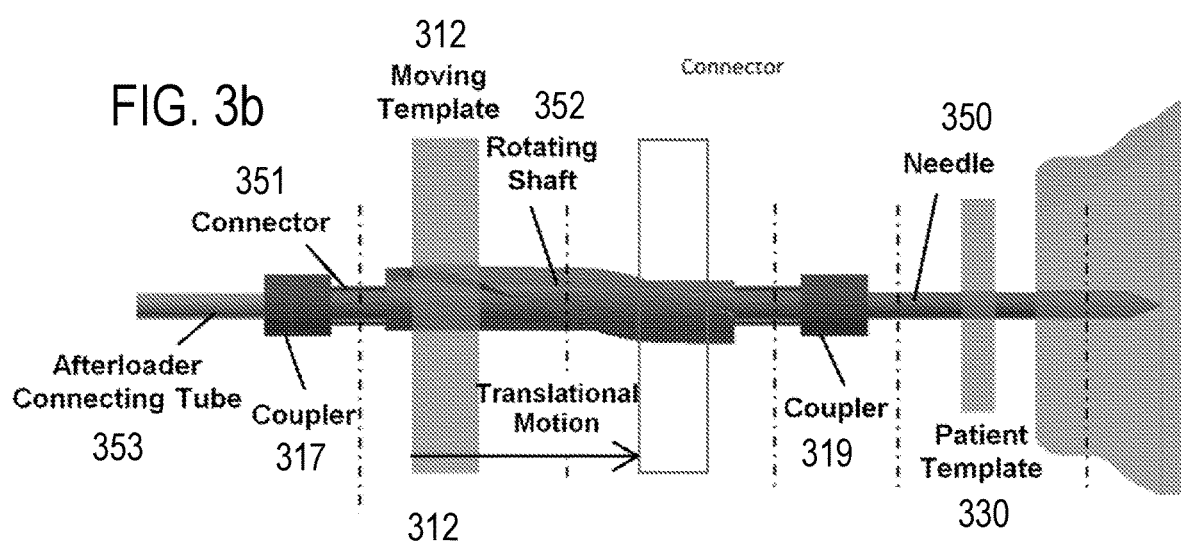
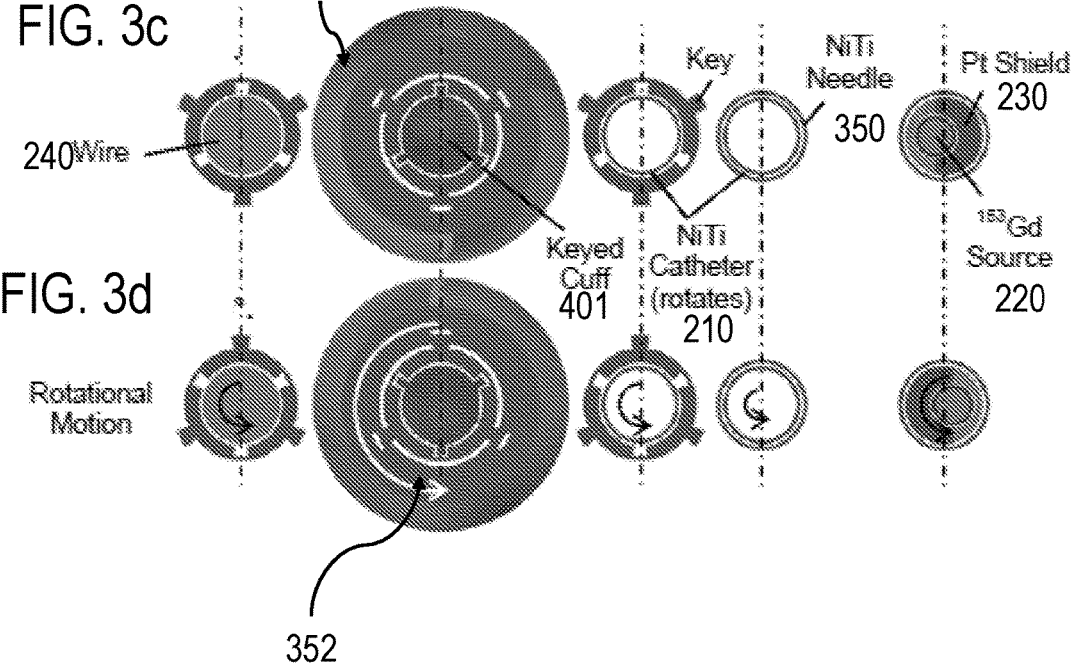

ROTATING SHIELD BRACHYTHERAPY SYSTEM

CROSS-REFERENCE TO RELATED APPLICATION

This application claims priority to U.S. Provisional Application No. 62/324,432 filed on Apr. 19, 2016. The aforementioned application is herein incorporated by reference in its entirety.

BACKGROUND OF THE INVENTION

Technical Field

The invention relates to the field of radiation oncology.

Related Art

Prostate cancer is the most common non-skin cancer in men, with 220,800 new diagnoses in 2015 in the U.S. Approximately 14% of men will be diagnosed with prostate cancer in their lifetime. Currently 82% of men diagnosed with prostate cancer receive surgery, brachytherapy, or external beam radiotherapy (EBRT). If healthcare trends develop such that all low-risk prostate cancer patients (48% of patients) receive active surveillance and 30% of those patients receive treatment within 5 years of diagnosis, estimates show that nearly 126,000 men diagnosed with prostate cancer in 2015 will receive treatment in the next five years.

Most prostate cancer patients have localized prostate cancer treated with a variety of treatment options including surgery, EBRT, low-dose-rate brachytherapy (LDR-BT), high-dose-rate brachytherapy (HDR-BT), chemotherapy, and combinations thereof. Although long-term (10+ year) biochemical disease-free survival is high and tends to increase with radiation dose delivered, 27,540 men in the U.S. are estimated to have died of prostate cancer in 2015. While achieving tumor control is paramount, prostate cancer patients may live with the side effects of their treatment for decades, and anticipated side effects play a strong role in treatment decisions. Treatment decisions are often based on anticipated side effects, such as urinary incontinence, urethral stricture, rectal bleeding, and sexual dysfunction. Existing treatments all have incidences of side effects that negatively affect patients' quality of life for decades at a significant cost to the healthcare system.

Brachytherapy is a radiotherapy technique in which radiation sources are placed inside of or adjacent to tumors, enabling the delivery of higher radiation doses than would be possible with EBRT, wherein radiation beams from outside the patient must pass through healthy tissues on the way to tumors. With brachytherapy, the radiation dose that can be delivered to tumors is still limited by the presence of adjacent healthy tissues. For prostate cancer, the urethra, rectum, and bladder limit tumor dose.

Existing brachytherapy techniques offer advantages over other treatments in both survival and side effects with the exception of increased urinary complications, highlighting a critical need for a lower-toxicity treatment technique. In a large-scale literature review (848 of 18,000 publications), Grimm et al (2012) found that in low-risk patients, brachytherapy provides: superior long-term (10+ year) biochemical relapse-free survival to EBRT and surgery; in intermediate-risk patients, brachytherapy alone is equivalent to EBRT in combination with brachytherapy and superior to surgery and EBRT alone; and in high-risk patients, EBRT in combination with brachytherapy is superior to more localized treatments such as surgery alone, brachytherapy alone, or EBRT alone. The benefits of brachytherapy in obtaining long-term relapse-free survival are suspected to be due to the dose escalation achievable that would not be possible with EBRT alone. Surgery, even using the Da Vinci robot (Intuitive Surgical, Inc., Sunnyvale, Calif.), has been reported to have greater risks of urinary incontinence and sexual dysfunction than radiotherapy techniques, in that brachytherapy has a 3-fold higher rate of return to baseline urinary function compared to surgery at 36 months, and it has a 5-fold higher rate of return to baseline sexual function. HDR-BT and combined EBRT and HDR-BT have equivalent or lower sexual dysfunction and gastro-intestinal toxicity than EBRT alone, but greater late grade ≥3 urethral stricture rates at 5 years of 7-10% versus 1-2% for EBRT alone.

A major limitation of conventional brachytherapy is that the radiation dose distribution delivered with brachytherapy sources is radially symmetric about the source axis, which limits the tumor dose conformity achievable. Further, in the radiation oncology field, increased radiation doses delivered in fewer treatment fractions, or hypofractionation, is becoming increasingly important both for improving patient care and reducing treatment cost.

Therefore is a critical need in the urology and radiation oncology fields for new and innovative prostate cancer treatment techniques with equal or greater cancer control probability than current techniques, and reduced toxicity, and overcomes the limitations discussed above while meeting the aforementioned goals.

SUMMARY OF THE INVENTION

In an aspect, the invention is an apparatus and method for using rotating shield brachytherapy (RSBT). In an aspect, RSBT can be used to maintain or increase tumor dose relative to conventional techniques, but with a dramatic reduction in radiation dose to the urethra, rectum, and bladder in the treatment of prostate cancer. In an aspect, with RSBT, partially shielded radiation sources can be placed in the prostate away from sensitive tissues.

In an aspect, the invention is an apparatus and method for the precise angular and linear positioning of multiple partially-shielded radiation sources in interstitial needles. The system enables the delivery of RSBT, for example to prostate cancer, using one or more radiation sources, including, but not limited to, a gadolinium-153 ($^{153}$Gd) radioisotope. The $^{153}$Gd source emits photons with ideal energies for partial shielding, but its low dose rate necessitates a multi-source approach for the delivery process in order for treatments to take place in a clinically reasonable timeframe of less than 2 hours. The system is designed primarily to treat prostate cancer with the goal of reducing dose to the urethra by 20-40% relative to conventional techniques, which is expected to significantly reduce the probability of complications.

In a further aspect, the invention comprises a catheter position verification and correction apparatus for the precise and simultaneous angular positioning of multiple shield-containing catheters in the RBST system. The apparatus can consist of an array of sensors to measure and correct for deviations between actual and desired catheter angular positions and depth in real time before and during treatment delivery. The system minimizes uncertainty in the dose distribution by maintaining the delivered catheter angles within a desired tolerance level for RSBT to be acceptable for clinical use. In embodiments, the system overcomes the challenge of positioning multiple shield-containing catheters simultaneously with appropriate accuracy to deliver RSBT. It affords a sufficient level of angular and depth robustness to the system (97% of points or higher at 3%/3 mm accuracy for actual versus planned dose distributions, for example) by positioning the catheters within a desired tolerance (±3 degrees in rotation and ±1 mm in depth, for example). The sensors, which can include cameras, are placed such that the catheter couplers are visible to the camera system. In addition, a covariance table based on regression analysis is developed to estimate the positions of any obscured catheters with high accuracy.

These and other objects and advantages of the invention will become apparent from the following detailed description of the preferred embodiment of the invention. Both the foregoing general description and the following detailed description are exemplary and explanatory only and are intended to provide further explanation of the invention as claimed.

The accompanying drawings are included to provide a further understanding of the invention and are incorporated in and constitute part of this specification, illustrate several embodiments of the invention, and together with the description serve to explain the principles of the invention.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 3b-d illustrate components of the RSBT delivery system of FIG. 2a.

Figure 1A:
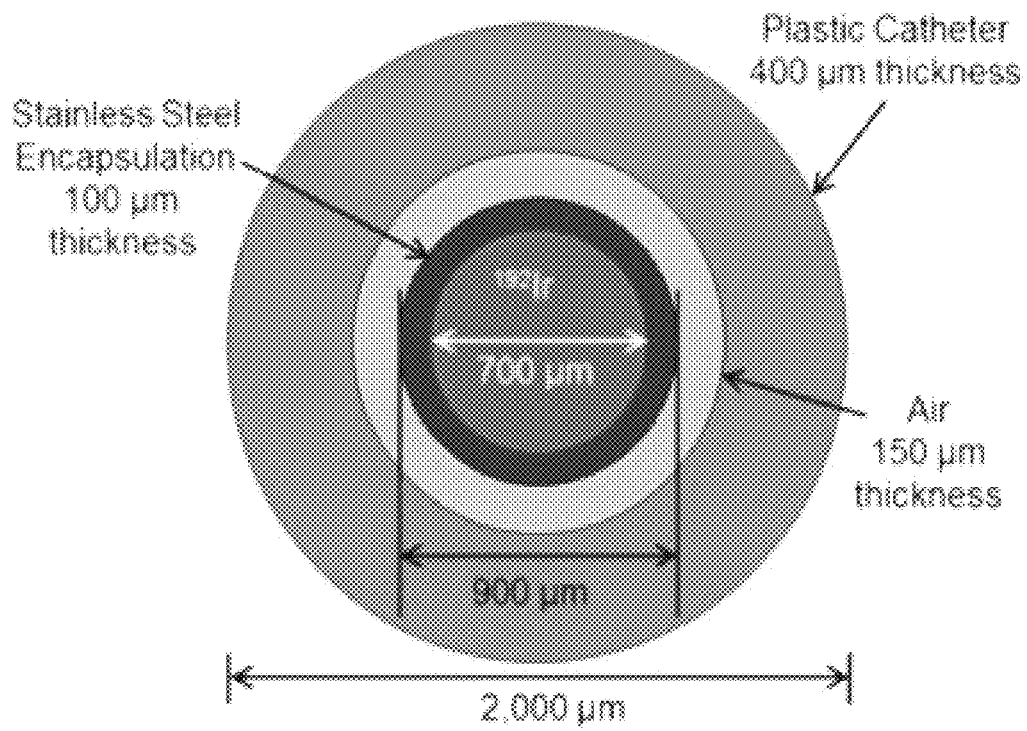
FIGS. 1a-h illustrate differences between conventional HDR-BT (top row) and $^{153}$Gd-based RSBT (bottom row). (a) Where a radially-symmetric applicator/source system is used for HDR-BT, (b) an applicator/source/catheter system with a spatially-offset $^{153}$Gd source and a platinum shield would be used for RSBT. The dose rate distributions from the sources, normalized to 100% at 1 cm off-axis, are radially-symmetric for (c) HDR-BT and (d) directionally-biased for RSBT. The resulting dose distributions have reduced doses to the urethra, rectum, and bladder, when the minimum dose delivered to the hottest 98% ($D_{98\%}$) of the prostate at a distance of 3 mm or greater from the urethra is held constant. For (e-f) 0 mm and (g-h) 3 mm urethral margins, RSBT reduced the minimum dose to the hottest 0.1 cm$^3$ of the urethra ($D_{0.1cc}$) by 29% and 38%, respectively. RSBT rectum and bladder $D_{1cc}$-values (complication predictors) were less than those for HDR-BT by 5-7%.
Figure 1B:
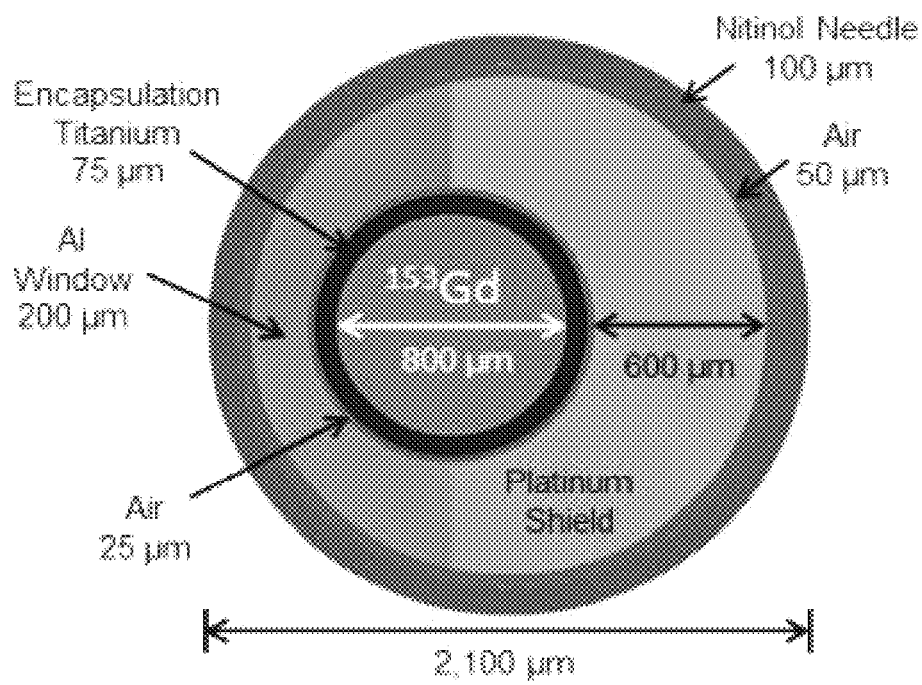
Figure 1C:
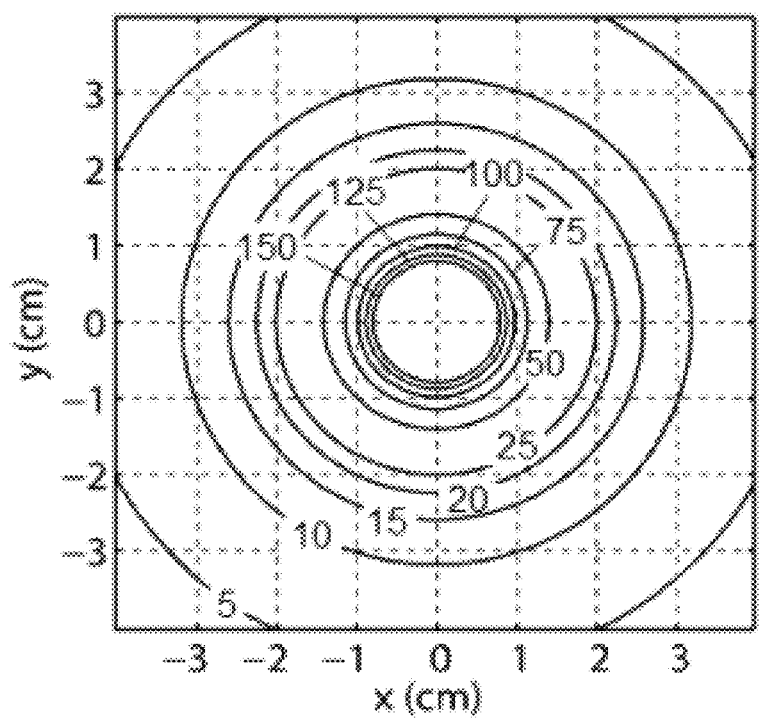
Figure 1D:
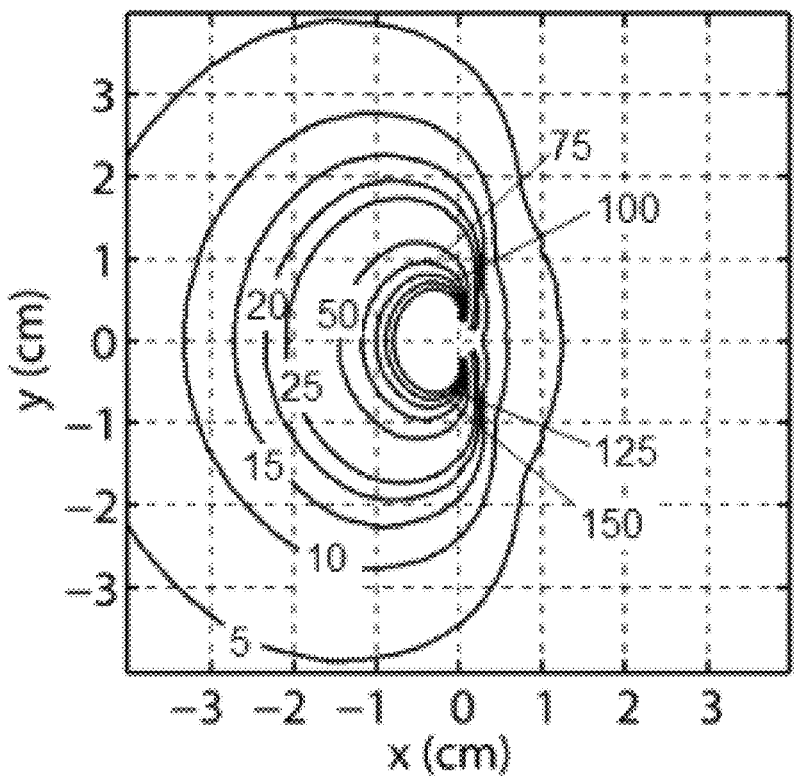
Figure 1E:
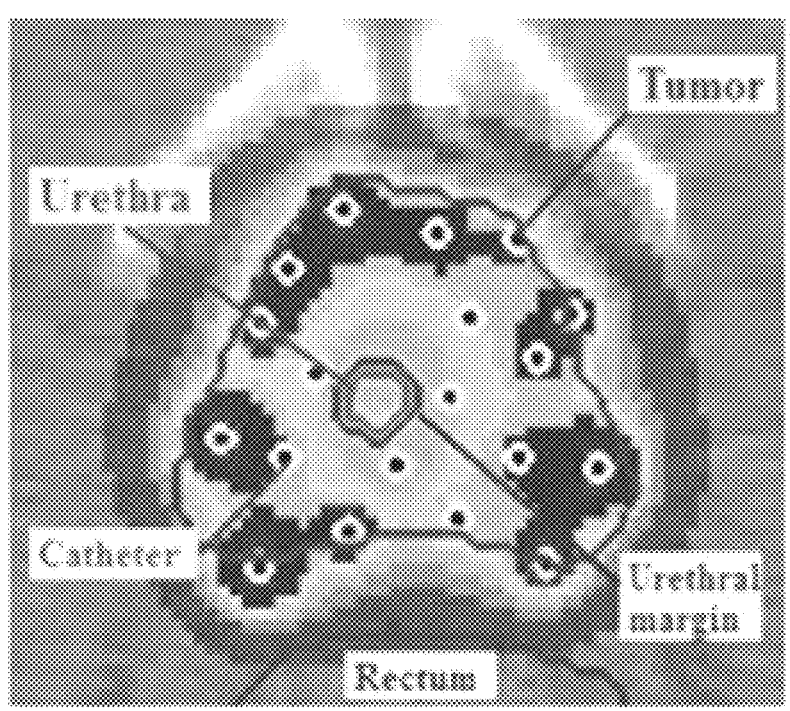

Other features of the present embodiments will be apparent from the Detailed Description that follows.

DETAILED DESCRIPTION OF THE INVENTION

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, aspects of the current invention may take the form of an entirely hardware embodiment, an entirely software embodiment, or an embodiment combining software and hardware aspects. In an aspect, the current invention can include a combination of physical components configured to perform certain steps and functions (e.g., controlling the linear and rotational movement of the RSBT sources, etc.) that are controlled by a combination of hardware and software components. Furthermore, components of the methods and systems may take the form of a computer program product on a computer-readable storage medium having computer-readable program instructions (e.g., computer software) embodied in the storage medium. Any suitable computer-readable storage medium may be utilized including hard disks, CD-ROMs, optical storage devices, or magnetic storage devices.

Further, components and methods utilized by the present invention as described below can be performed in a program environment, which may incorporate a special purpose device, such as a hardware appliance, controller, or hand-held computer. In addition, the techniques of the components described herein can be implemented using a variety of technologies known in the art. For example, the methods may be implemented in software executing on a computer system, or implemented in hardware utilizing either a combination of microprocessors or other specially designed application specific integrated circuits, programmable logic devices, or various combinations thereof.

Some aspects of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer readable memory that can direct a computer or other programmable data processing apparatus to function in a particular manner, such that the instructions stored in the computer-readable memory produce an article of manufacture including computer readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions, and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

In an aspect, the invention is a RSBT system and method, as illustrated in FIGS. 2-22. In an aspect, a rotating shield brachytherapy (RSBT) system 100 can be used to overcome limitations of conventional brachytherapy. FIGS. 1a-h illustrate a comparison of conventional high-dose-rate brachytherapy (HDR-BT) to an embodiment of a RSBT system, with FIGS. 1a, c, e, and g illustrating HDR-BT, and FIGS. 1b, d, f, and h illustrating RSBT. A RSBT system 100 can utilize a RSBT delivery device 200. The RSBT delivery device 200, which includes a combination of a radiation shield 230 and radiation window 222 contained within a catheter 210, is used to partially occlude the brachytherapy source 220, as shown in FIGS. 2, 3c-d, and 4, producing a deliberately non-radially-symmetric radiation dose distribution about the source 220. During RSBT delivery, the radiation shield 230 moves dynamically about the radiation source 220, such as a $^{153}$Gd, directing radiation away from healthy sensitive tissues and into tumor tissues through the radiation window 222. In addition, the radiation shield 230 can include a distal cap 232, which blocks radiation in the distal direction. In an aspect, the radiation window 222 is comprised of aluminum. In other aspects, various other materials that allow for the passage of radiation can be used for the window 222. The RSBT delivery device 200 can thus deliver far greater radiation doses to the tumor for a given healthy tissue dose, enabling dose escalation to the tumor and increasing tumor control probability. RSBT can also be used to deliver the same radiation doses to tumors as is delivered conventionally, while substantially reducing the radiation dose delivered to healthy tissues with the goal of reducing side effects relative to conventional brachytherapy. While the RSBT system 300 discussed below has been shown to have clinical benefits specifically prostate cancer, the RSBT system 300 can also be utilized for treatment of various other types of cancer in which OAR are a significant factor to the treatment.

In an aspect, the RSBT system 300 and methods can be used to maintain or increase tumor dose relative to conventional techniques, but with a dramatic reduction in radiation dose to the urethra, rectum, and bladder in the treatment of prostate cancer. In an aspect, with the RSBT system 300, partially shielded radiation sources 220, contained within the catheter 210, can be placed in the prostate away from sensitive tissues. In an exemplary aspect, partially-shielded (i.e., the combination of the shield 230 and window 222) $^{153}$Gd (240 day half-life, 60.9 keV average photon energy) radiation sources 220 can be utilized (see FIG. 2). However, other radiation sources (i.e., active isotope(s)) can include, but are not limited to, Ir-192, Gd-153, I-125, Cs-131, Cs-137, Pd-103, Yb-169, or Co-57, and the like.

Conventional HDR-BT systems utilize unshielded conventional $^{192}$Ir (74 day half-life, 360 keV average energy). In an aspect, $^{192}$Ir emits photons with energies too high for interstitial RSBT (FIGS. 1a,c), whereas $^{153}$Gd has an appropriate photon spectrum for partial shielding. In an aspect, the $^{153}$Gd source can use Gd-3NO$_3$ (gadolinium trinitrate, a powder), which contains between 1-3.2 TBq/g of $^{153}$Gd, and is commercial available. In an aspect, the $^{153}$Gd source 220 can use gadolinium oxide, gadolinium chloride, and other forms of $^{153}$Gd (e.g., pellets or metal). In an exemplary aspect, the formation discussed above can have $^{153}$Gd activity that emits photons in the range of 40 to 105 keV. However, in other aspects, the activity can have ranges that exceed that discussed above. The $^{153}$Gd source 220 can be loaded into a capped (e.g., the distal cap 232) nitinol tube/catheter 210 with a 10 mm active length.

In an aspect, as discussed above, the radiation source 220 is placed within a catheter 210 of the RSBT delivery device 200, including the radiation shield 230 with a distal cap 232, and a radiation window 222, as shown in FIGS. 2, 3c-d and 4. In an aspect, the radiation shield 230 can be comprised of materials that have high atomic numbers that are configured to block radiation in a highly effective manner, including, but not limited to, platinum, iridium, gold, silver, lead, tungsten, osmium, and the like. The radiation window 222 can be comprised of materials that allow radiation to pass through at a known rate while providing some protection, including, but not limited to aluminum.

In an exemplary aspect, the combination of a $^{153}$Gd source 220 with a platinum shield 230 of approximately 600 microns thick has enough shielding to reduce the transmission of radiation to about 5% on the other side of the shield 230 and create a radially non-isotropic asymmetric dose distribution in order to selectively avoid the urethra, rectum, and bladder during the irradiation process. In this aspect, the approach is able to reduce the maximum urethral dose by 20-40% relative to the conventional high-dose-rate brachytherapy approach. This is achieved by using multiple $^{153}$Gd sources 220 that are individually shielded with high atomic number, high-density, shields 230, as shown in FIG. 3a, discussed in detail below.

In an aspect, a wire 240 (see FIG. 3c) can be utilized with the RSBT delivery device 200 discussed above. For example, a wire 240 made of stainless steel or nitinol can run the length of the nitinol catheter tube 210 to connect the source/shield capsule (220/230) to the source wire 240 proximal to the nitinol catheter tube 210. The wire 240 running the length of the nitinol tube 210 would act as a safety mechanism to ensure the source 220 and shield 230 can be retracted in the event that the nitinol tube/catheter 210 breaks inside a needle (discussed below) used for RSBT delivery.

Figure 2:
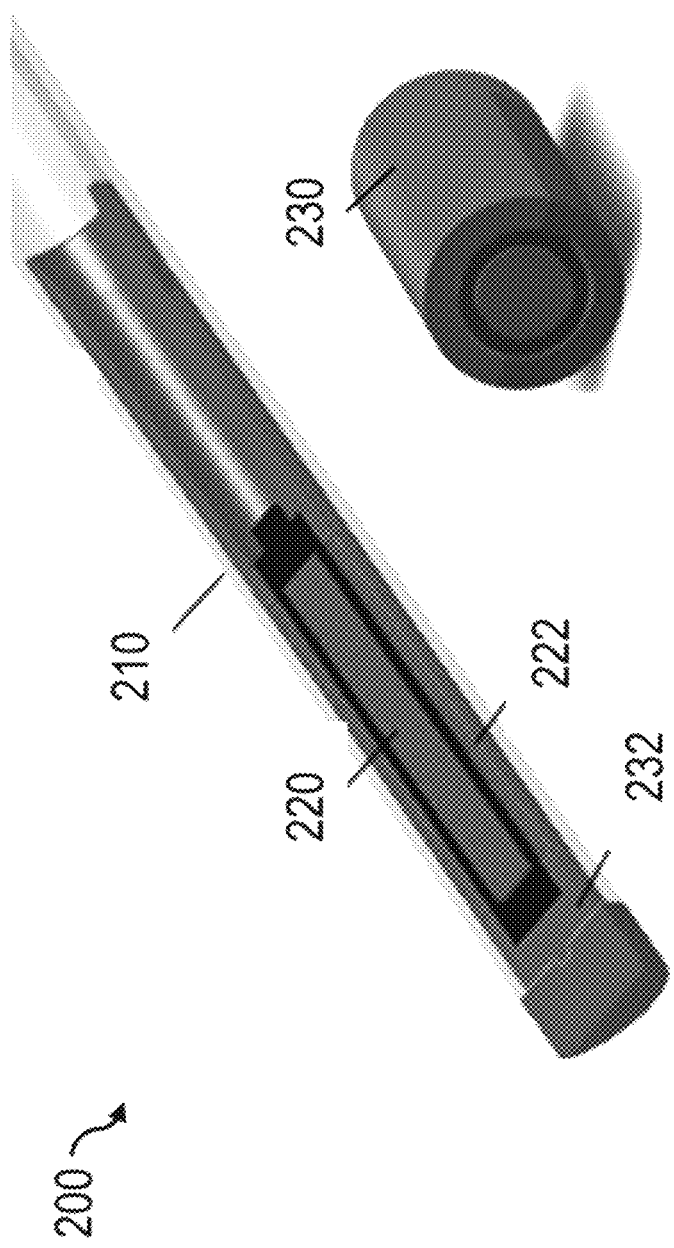
FIG. 2 illustrates a shielded catheter with 4 mm diameter for $^{153}$Gd source catheter (2 mm diameter, 5.55 GBq according to an aspect of the present invention).
Figure 3A:
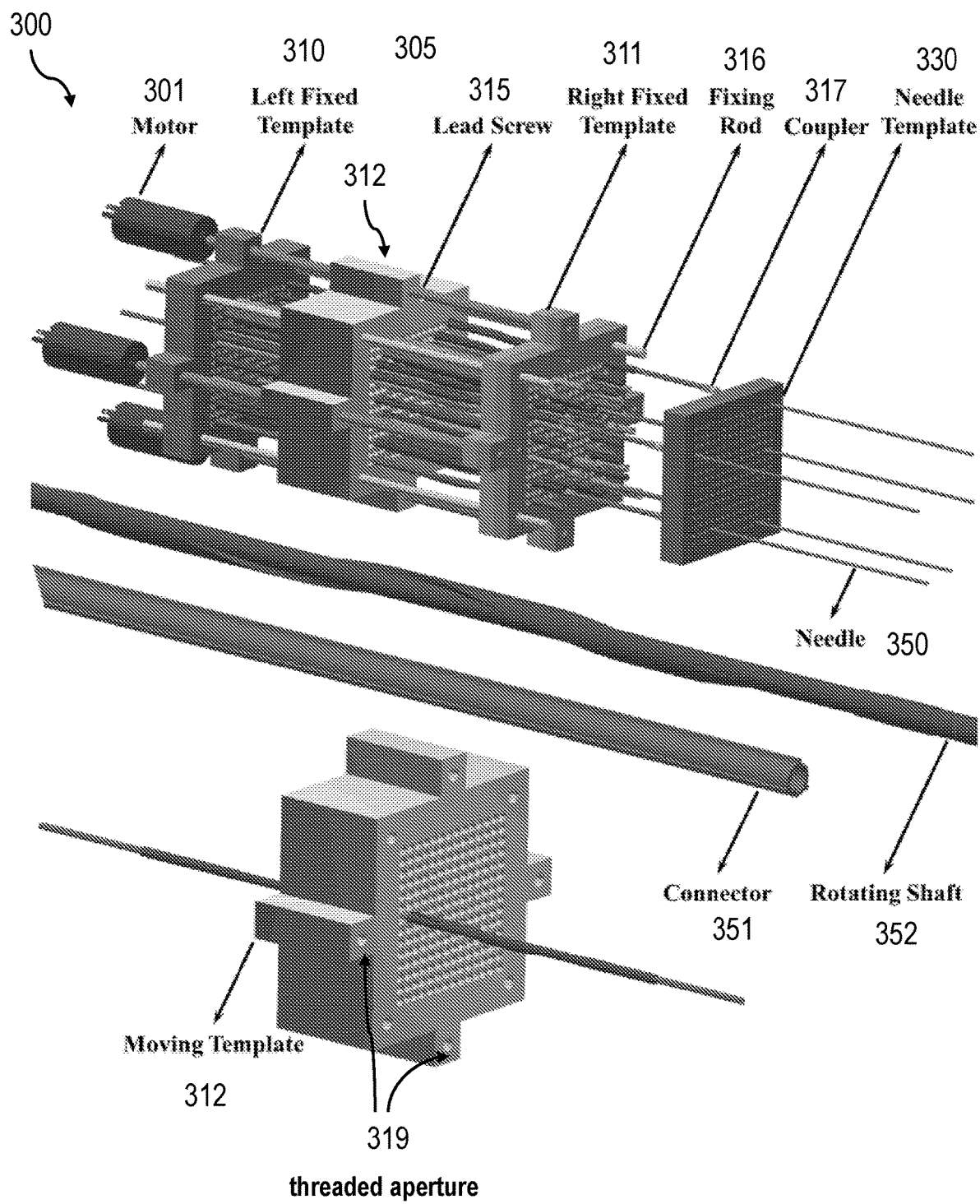
FIG. 3a is a schematic representation of the RSBT delivery system according to aspects of the present invention.
Figure 4:
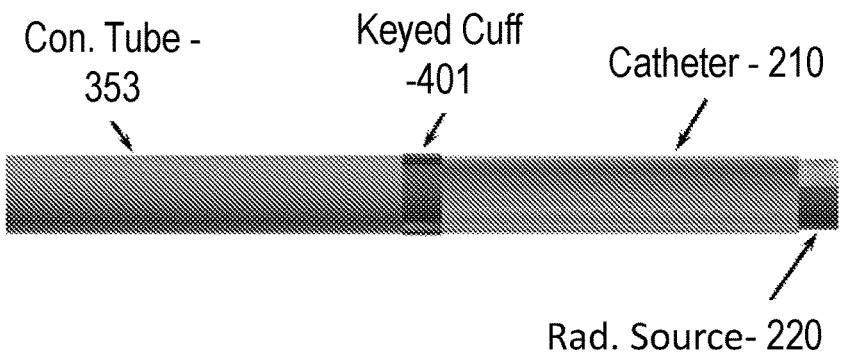
FIG. 4 illustrates a schematic representation of a shielded source within a catheter within a needle mounted to a keyed cuff mounted to an afterloader connecting tube according to an aspect.

In an additional aspect, the RSBT system 100 can include a catheter 210 (or other applicator) configured to contain the radiation source 220, as shown in FIGS. 2 and 3a-b. In an aspect, the catheter 210 is configured to fit into an applicator. In an aspect, the catheter 210 can include a needle 350 (See FIGS. 2a-d). In an aspect, the catheters 210 and needles 350 can be formed from nitinol. Different materials than nitinol, such as plastic or stainless steel, or combinations, could theoretically be used for the catheters 210 and needles 350, although the wall thicknesses and flexibility of the catheters 210 and needles 350 may not be as optimal as with nitinol. In an aspect, the nitinol needle 350 can be formed by welding a sharp nitinol cone to an end of a 16 gauge nitinol tube. In an aspect, the emission window 222 is configured to be connected, welded, coupled, or adjacent to the platinum shield 230 and distal cap 232 and inserted into the nitinol catheter 210 (see FIGS. 2, 3c-d and 4). In an exemplary aspect, the emission window 222 is made from aluminum. In an aspect, the shield 230 and aluminum emission window 222 are laser-welded into place.

The RSBT system 100 is configured to deliver high radiation doses (10-20 Gy)(although other dosages could be used depending on the clinical need) to the prostate per session in very few (1-3) outpatient visits, which reduces the overall cost of prostate cancer therapy relative to conventional treatments by increasing treatment efficiency and minimizing side effects. Partial shielding 230 (shown in FIG. 1b) enables a deliberately non-symmetric dose distribution (shown in FIG. 1d) about an implanted needle 350, providing the opportunity to shield healthy tissues from radiation damage. The shielded RSBT delivery devices 200, and more specifically the catheter 210 containing the radiation source 220 within a shield 230, move dynamically inside the prostate in a manner that reduces the dose delivered to the rectum, bladder, and urethra relative to conventional HDR-BT without compromising the tumor dose (FIG. 1e-h).

Figure 1F:
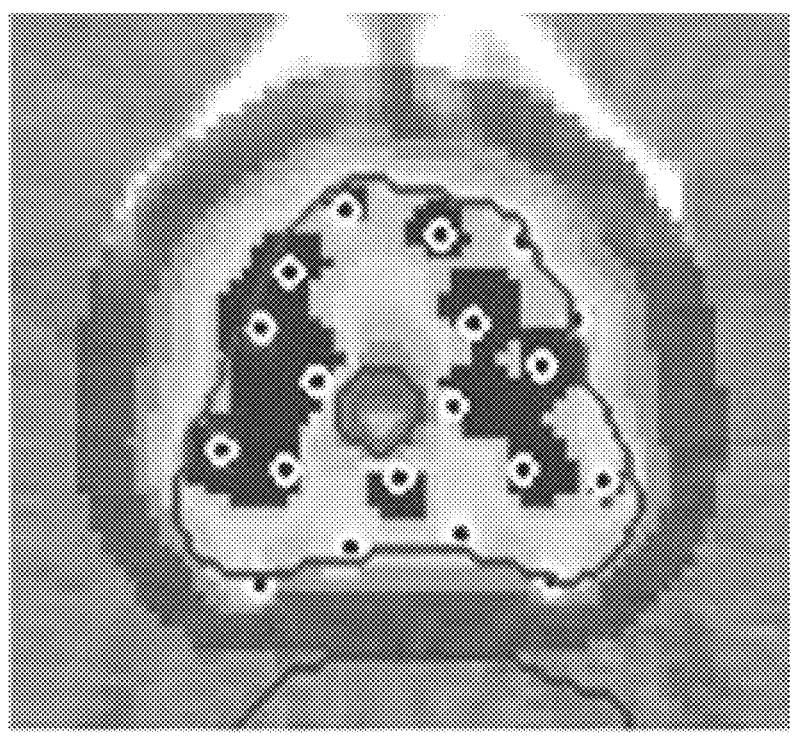
Figure 1G:
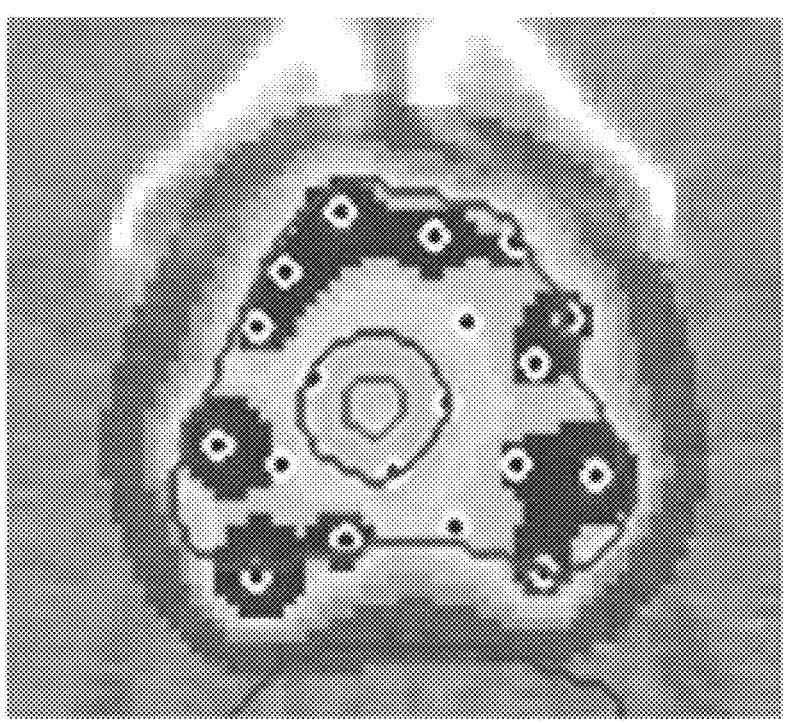
Figure 1G:
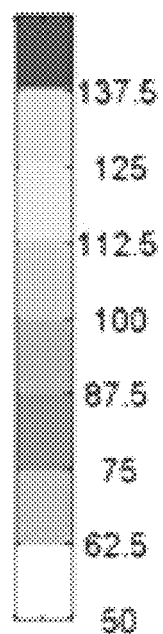
Figure 1H:
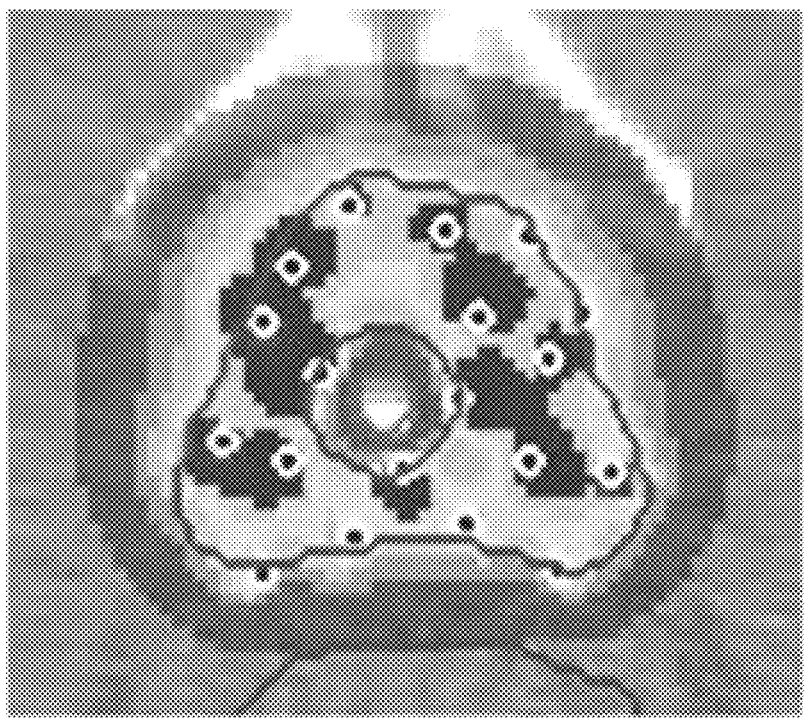
Figure 1H:
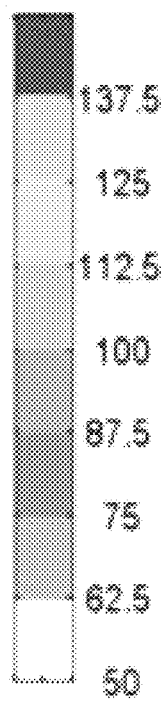

In an aspect, and discussed in more detail below, multiple needles 350 can be utilized at the same time, each containing a RSBT delivery device 200 (see FIGS. 1f and h and 2a). In an exemplary aspect, approximately between 15-20 needles 350 containing a RSBT delivery device 200 (i.e., the catheter 210 containing the radiation source 220, emission window 222, and shielding 230) can be utilized. In another aspect, the catheters 210 can be configured to be slowly and incrementally rotated through treatment to deliver the desired dose distribution, with the dwell times within each catheter 210 modulated so that radiation is emitted for a longer time in some directions (i.e., into the tumor) than others (i.e., into OARs). The RSBT approach thus overcomes the limitations the rectum, bladder, and urethra impose on the dose deliverable to the prostate with conventional HDR-BT, which constrain prostate dose.

Reducing urethral dose reduces toxicity, and the reduction of a 9.5 Gy per treatment fraction (2 normal fractions delivered by HDR-BT dose) to 6 Gy per fraction (3 fractions delivered)—a 37% dose-per-fraction reduction—reduced grade ≥2 urethral stricture rates by 29 percentage points (32% vs. 3%) in a clinical study. See Hindson, Millar, and Matheson (2013). RSBT-based dose escalation enabled by enhanced healthy tissue sparing has the potential to improve cure rate because biochemical disease-free survival increases with prostate dose. In the radiation oncology field, increased radiation doses delivered in fewer treatment fractions, or hypofractionation, is becoming increasingly important both for improving patient care and reducing treatment cost. The RSBT approach is consistent with the field's direction and will have a major impact on the treatment of prostate cancer.

In an aspect, with $^{153}$Gd having a lower dose rate than $^{192}$Ir, RSBT delivery can take longer than the 30 minutes or less required for HDR-BT. According to an aspect, the RSBT system 100 of the present application employs several controlled simultaneously $^{153}$Gd sources 220 at once. Each source 220, contained within the catheter 210 and embedded in the shield 230 and emission window 222, is placed in its own interstitial needle 350 in the patient. In an aspect, the RSBT system 100 employs simultaneously controlled 62 GBq (1.5 Ci) $^{153}$Gd sources 220, enabling the delivery of a 10 Gy dose in an about 60 minutes. While the procedure times are increased, they are clinically acceptable primarily due to the clinical advantages RSBT can provide. This has been the case for cervical cancer brachytherapy guided by magnetic resonance imaging, where an increase in complexity and procedure time (1-3 hours) are accepted to improve outcomes in patients with bulky (>5 cm) tumors.

In an aspect, the RSBT system 100 further comprises a RSBT delivery system 600, the components of which are illustrated in FIGS. 3-8. In an aspect, the RSBT delivery system 600 is configured to control the rotational and translation of the nitinol catheter-mounted sources/shields 220/230 for all implanted needles 350 simultaneously. In an aspect, there are multiple (twenty, for example) shielded catheters 210 inserted into the patient's perineum, each of which can rotate independently. The catheter 210 can be connected to an afterloader machine 601, such as the ones shown in FIGS. 6-7, containing the radioactive source 220 that is pushed down automatically toward inside of the needle 350, while the platinum shield 230 is rigidly attached to it.

As shown in FIGS. 3a-d, the RSBT delivery system 600 is comprised of several components, including a multi-source RSBT apparatus 300, a multi-source remote afterloader 601, and additional components discussed below. The RSBT delivery system 600, via the multi-source RSBT apparatus 300, can include a plurality of nitinol needles 350 configured to contain the shielded radiation sources 220/230 discussed above. The nitinol needles 350 are configured to be received by apertures within a needle template 330, also referred to as a patient or human template 330 (FIGS. 3a-b). The needle template 330 provides a holding mechanism for the needles 350 in the appropriate position when they are inserted into the patient's body.

Each needle 350 is coupled to an afterloader connecting tube 353 (see FIGS. 3b and 4) by a connector 351 (See FIGS. 3a-b), which passes through a rotating shaft 352 (not all shown)(see FIGS. 3a-d). The catheters 210 containing the radiation source 220, which travel inside the connecting tubes 353, are moved back and forth by linear actuators (discussed below) to all of the necessary depths in each needle 350. In an aspect, the RSBT delivery system 600 includes a multi-source afterloader 601 that controls the depth of the radiation source 220 in each needle 350 (See FIGS. 6-7). In an aspect, couplers 317, 319 (FIG. 3b) are used to connect the needle 350 and the afterloader connecting tube 353 to the connector 351. The connector 351 has the leeway to move freely back and forth through the rotating shaft 352 in order to get connected to the needle 350 implanted into the patient via a second coupler 319. The connector 351 has a key role in the whole procedure as the connector 351 can slide in and out of the rotating shaft 352 enabling a rigid connection between the afterloader connecting tube 353 and the implanted needles 350 which protrude from the patient at different lengths. Thus, the needles 350 do not have to be inserted in the same depth in the patient.

The connectors 351 extend through apertures of three templates, a left fixed template 310, a right fixed template 311, and a moving template 312 located between the left fixed template 310 and right fixed template 311 (FIG. 3a). The fixed templates 310, 311 provide rigidity to the RSBT delivery system 600. The apertures of the moving template 312 and fixed templates 310, 311 correspond to the apertures in the needle template 330. The large number of apertures in the templates 310, 311, 312, 330 provides the physician with the flexibility to select the most appropriate apertures/holes (approximately 20) that best fit the patient need and the clinical target volume (CTV) shape. The number of apertures in the templates 310, 311, 312, 330 can vary. However, in the preferred embodiment, each template 310, 311, 312, 330 has approximately the same number of apertures organized/aligned in communication with one another.

Figure 6:
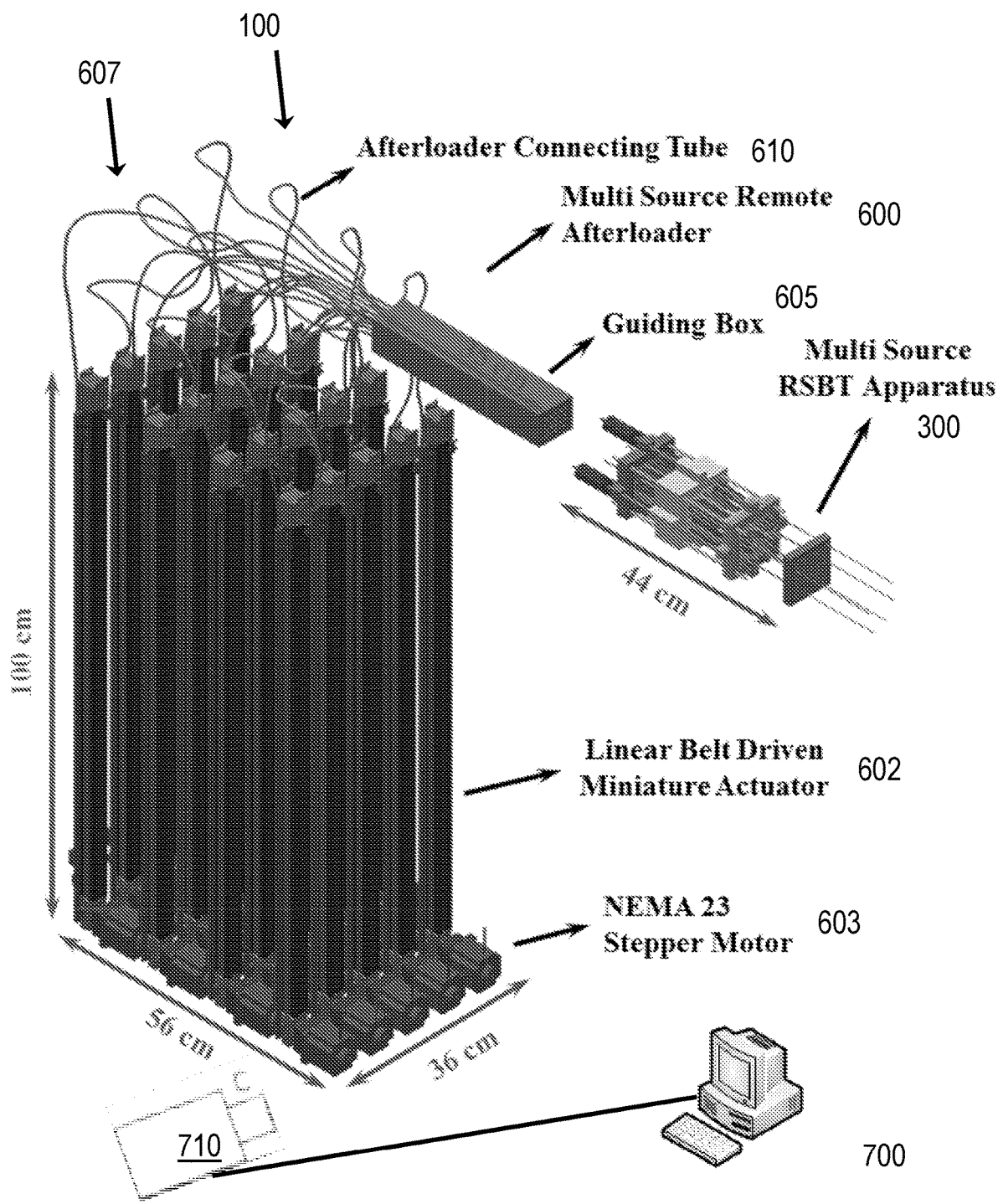
FIGS. 6-7 illustrate components of the RSBT delivery system, including a remote afterloader, according to an aspect of the present invention.
Figure 7:
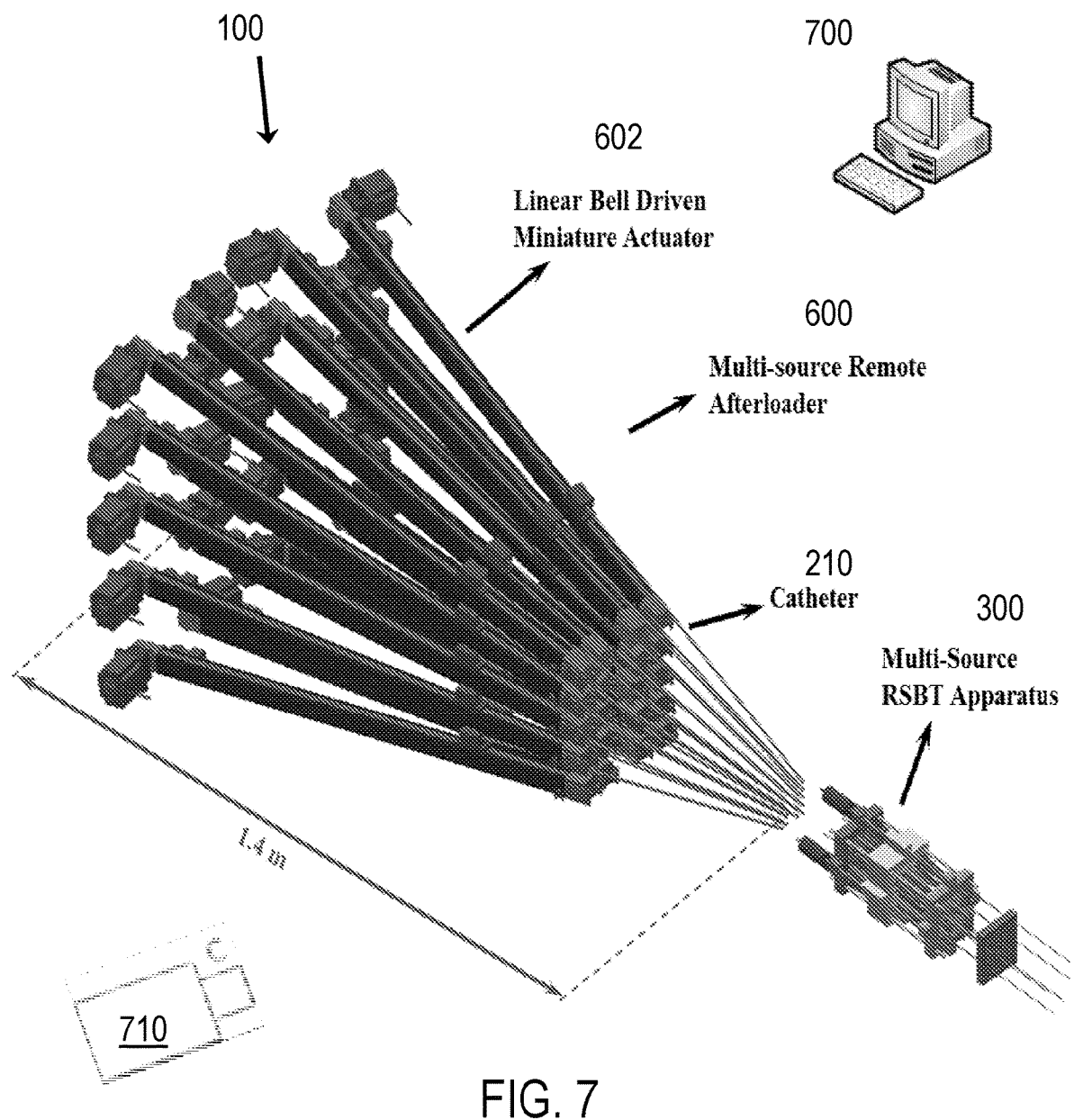

The moving template 312 is slidably mounted on rods 316 anchored to the left fixed template 310 and right fixed template 311 (See FIG. 3a). In addition, the moving template 312 interacts with at least one lead screw 315 via at least one threaded aperture 318, where the lead screw 315 drives the translation of the moving template 312 when activated. In an aspect, as shown in FIGS. 3a and 6-7, four rods 316 and four lead screws 315 are used to translate the moving template 312 between the left fixed template 310 and right fixed templates 311. The lead screws 315 can be driven by motors 301. The motors 301 can include, but are not limited to, step motors, linear motors, piezoelectric motors, encoded motors, rotational motors and the like. Multiple motors 301 can be used. For example, a combination of four motors 301 and four lead screws 315 can be utilized to drive the moving template 312.

In an aspect, all needles 350, afterloader connecting tubes 353, and connectors 351 have the same lengths as each other. As shown in FIGS. 3c-d, some of the cross sections of the mechanical parts discussed above contain keys machined in them that dictate the entire radiation shield 230 to be oriented at a known angle. In an aspect, the catheters 210 are rigidly attached to a proximal keyed cuff 401 (see FIGS. 3c-d and 4). The keyed cuff 401 matches parallel recesses along the interior surface of the connector 351. The combination of the keyed cuff 401 and the matching recesses within the connector 351 enables the angular orientation of the shielded source 220/230 to be fixed and known at all times during treatment. Further, the outer surface of the connector 351 is keyed to match parallel recesses found within the inner surface of the rotating shaft 352 (See FIGS. 3a-d and 5).

In addition, the outer surface of the rotating shaft 352 includes at least one helical key 352a that engages recesses found within the apertures of the moving template 312. This configuration leads to the rotation of the catheter 210 as the outer shaft 352, as the helical key 352a engages a keyed portion of the apertures of the moving template 312, thereby rotating the rotating shaft 352, which in turn rotates the connector 351, and the catheter 210 through the keyed cuff 401. In an aspect, all rotating shafts 352 are locked at the same angular orientation at a given time by the moving template 312, which, when translated, simultaneously rotates all of the shafts 352. The way that the combination of moving template 312 and shafts 352 brings about the desired source 220 and shield 230 rotation is as follows: when the moving template 312 is translated longitudinally, owing to the resistive friction between the shaft 352 and the helical key 352a and interior wall of apertures of the moving template 312, the longitudinal translation of the moving template 312 causes the shaft 352 to rotate as it applies pressure to the threaded exterior peripheral wall 352a of the shaft 352. The moving template 312 is translated by the motors 301 that are attached to the lead screws 315, and the shaft angular positions are well-known based on the position of the moving template 312. In this case, FIG. 3c shows the embodiment before translation of the moving template 312 and FIG. 3d shows the combination in which the moving template 312 is translated forward enough to have a 180° rotation of the shaft 352. In order to operate properly, the threaded shaft 352 has to be large enough in diameter to exert enough torque on the connectors 351 and the needles 350 in order to rotate them.

Figure 5:
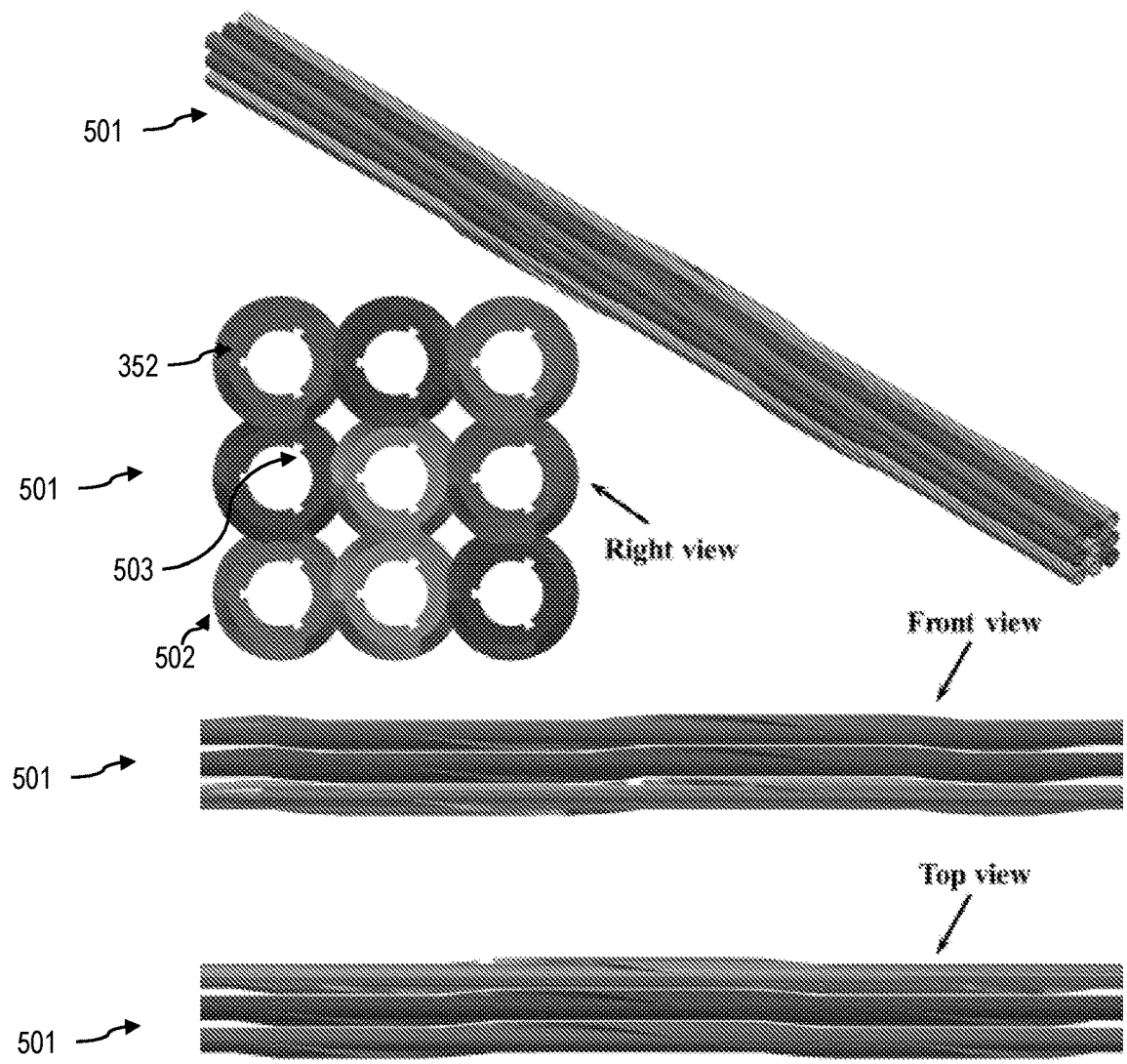
FIG. 5 illustrates a plurality of rotating shafts utilizing a moving tessellation theory according to an aspect of the present invention.

In an aspect, in order to maximize the diameters of the rotating shafts 352 under the constraint that the spacing between shaft centers must be at most 5 mm, a "moving tessellation" approach is utilized. Based on the tessellation theory, one type or more than one type of shapes can be geometrically designed such that if they are stacked on top and besides each other, no space in between the different shapes remains unused. As FIG. 5 shows, the design of the rotating shafts 352 approximately follows this particular geometric theory. The bundles 501 of rotating shafts 352 have outer surfaces 502, including the helical key 352a, that are contoured to the geometry having the tessellation property. The inner surfaces 503 of the rotating shafts 352 contain grooves to connect to the outer surface of the connectors 351. The main advantage of this design approach is that all of the radiation sources 220 are always pointed in the same direction. Otherwise the delivery technique would be highly susceptible to errors in which one or more sources 220 are oriented in the wrong direction during the treatment. Moreover, this tessellation pattern facilitates the optimal usage of the very limited space. In an aspect, the longitudinal length of the helical shaft key 352a must be less than half the pitch times 360 degrees. Thus, if the pitch is 0.278 mm per degree (10 cm per helical key rotation), then the longitudinal length of the shaft key 352a must be less than 5 cm.

The delivery then takes place as follows: the needles 350 are inserted inside the patient. Then the RSBT delivery devices 200, via the catheters 210, are docked on the implanted needles 350 via the couplers 317. The RSBT system 100 can be supported, for example, on the patient table, on a stand between the patient table and the afterloader 600, or on a robotic arm that attaches to the patient table, the floor, or the afterloader 601. In an aspect, a multiple source afterloader 600 is then used that simultaneously and independently controls the depths of all of the sources 220. The delivery process occurs by having the moving template 312 control the directions of all the needles 350 and using the afterloader 601 to control the angular position of all the sources 220 in all the needles 350 simultaneously. For each rotation angle, source depth of the source 220 in each needle 350 is controlled by the multi-source afterloader 600. An example of a multi-source remove afterloader 600 is shown in FIGS. 6-7. In such aspects, the multi-source remote afterloader 600 is an array of belt-driven linear actuators 602 to which the source wires 240 are mounted. Once the source angles are changed by translating the moving template 312, the multi-source afterloader 601 moves the sources 220 to all of the necessary depths in each needle 350.

In an example of operation of the RSBT system 100 according to an aspect, to keep delivery as simple as possible, all of the needles 350 are held at the same rotation angle at a given time, and the catheters 210 are rotated by translating the moving template 312 between the two stationary templates 310, 311. The translation of the moving template 312 causes the rotating shaft 352, and its helical key 352a, move within the keyed aperture (which has matching recesses for the keys) of the moving template 312. Since the rotating shaft 352 has a helical key 352a, the rotating shaft 352 rotates as the key 352a matches with the keyed aperture. In an exemplary aspect, during RSBT, the catheters 220 are rotated by 22.5° every 3-4 minutes, and only a single 360° rotation is needed for a full treatment. The process is repeated for all of the source rotation angles, and, if one were to use 16 different dwell positions with 16 different shield directions, all of the CTV would be covered while the urethra, rectum, and bladder are spared. The source 220/shield 230 for each needle 350 can be retracted back into the afterloader 600, and more specifically the guiding box 605 within less than 10 seconds in the event of an emergency. This would be done by moving all of the RSBT delivery devices 200 on the linear actuators 602 on the afterloader 601 to their home positions. The sources 220 would be retracted into the shielded guiding box 605 shown in FIG. 6. In an aspect, the guiding box 605 is also made of a material that blocks radiation.

In an aspect, the combination of radiation sources 220 and shields 230 such as $^{153}$Gd and platinum shields 230 are stored in the multi-source afterloader 600, shown in FIGS. 6-7. The multi-source afterloader 600 includes a plurality of actuators 602. In an aspect, the afterloader 600 includes twenty actuators 602. In an exemplary aspect, the afterloader 600 includes twenty identical commercially available LCR series linear miniature belt-driven actuators 602 that have positioning accuracy of less than ±0.2 mm. As shown in FIG. 6, four stacks of five identical LCR30 linear actuators 602 are assembled in a vertical orientation. A flexible wire 607 from each of those actuators 602 is fed into a guiding rigid box 605 in which the source/shield 220/230 combination and the nitinol catheters 210 are inserted and would be connected to the wires 240 by means of a coupler. Guide tubes (not shown) can be used to guide the wires. This orientation helps to diminish the occupying horizontal space of the whole multisource remote afterloader 600 which is preferred to be designed clinic-friendly and less spacious. However, as illustrated in FIG. 7, the nitinol catheters 210 can be translated into the multi-source RSBT apparatus 300 in the absence of any flexible wire and rigid guiding box. The practical challenge associated with this type of orientation is the huge space dedicated in the procedure room which might not be designed to incorporate everything longitudinally in a sequence.

In an aspect, a catheter position verification and correction system 700 is a component of the RSBT delivery system 100. The catheter position verification and correction system 700 can include at least one camera 710 configured to monitor the catheters 210 and provide feedback to a control system 750 based upon the position of the catheters 210 (rotational and transitional) within the patient. In an exemplary aspect, the catheter position verification and correction system 700 is capable of mechanically positioning the catheters 210 within 1 mm, 1 degree spatial accuracy and capable of verifying and correcting the catheter position inside an applicator/needle 350 to within 1 mm, 1 degree. In a further aspect, the RSBT system 100 can be configured to position, verify, and correct the multiple catheters in real time. In an aspect, the RSBT system 100 uses the catheter position verification and correction system 700 to deliver a clinical, multi-catheter prostate cancer RSBT radiation dose distribution. The catheter position verification and correction system 700 ensures the placement of the catheters 210, and more importantly the source 220 and window 222 placement, to prevent radiation overexposure to the OAR and underexposure to the tumor target.

In an aspect, the catheter position verification and correction system 700 can verify the delivered catheter angles within a 6° tolerance for RSBT, which is acceptable for clinical use. In an aspect, the coupler 317 (FIGS. 3c-d and 4) that rotates with the connector 351 and is attached to the needle 350 has angular patterns etched onto the wall that are easily detectable by the camera. The camera 710 can be an off-the-shelf camera, including, but not limited to, a Raspberry Pi camera module with 2592×1944 pixel resolution and passive auto-focus. Single or multiple cameras 710 can be employed to monitor the catheters 210. At a range of 5 cm, the field of view for the camera 710 is approximately 5 cm and the pixel size is 25 µm. The system 700 would thus be capable of determining the angular position of a 3 mm diameter coupler 317 to within 1°. In an aspect, a pattern recognition software based on the Canny method for finding the etched edges and utilizing a point-to-point registration operation is used to determine where the camera's field of view is on the coupler's surface in a polar coordinate system.

Figure 16:
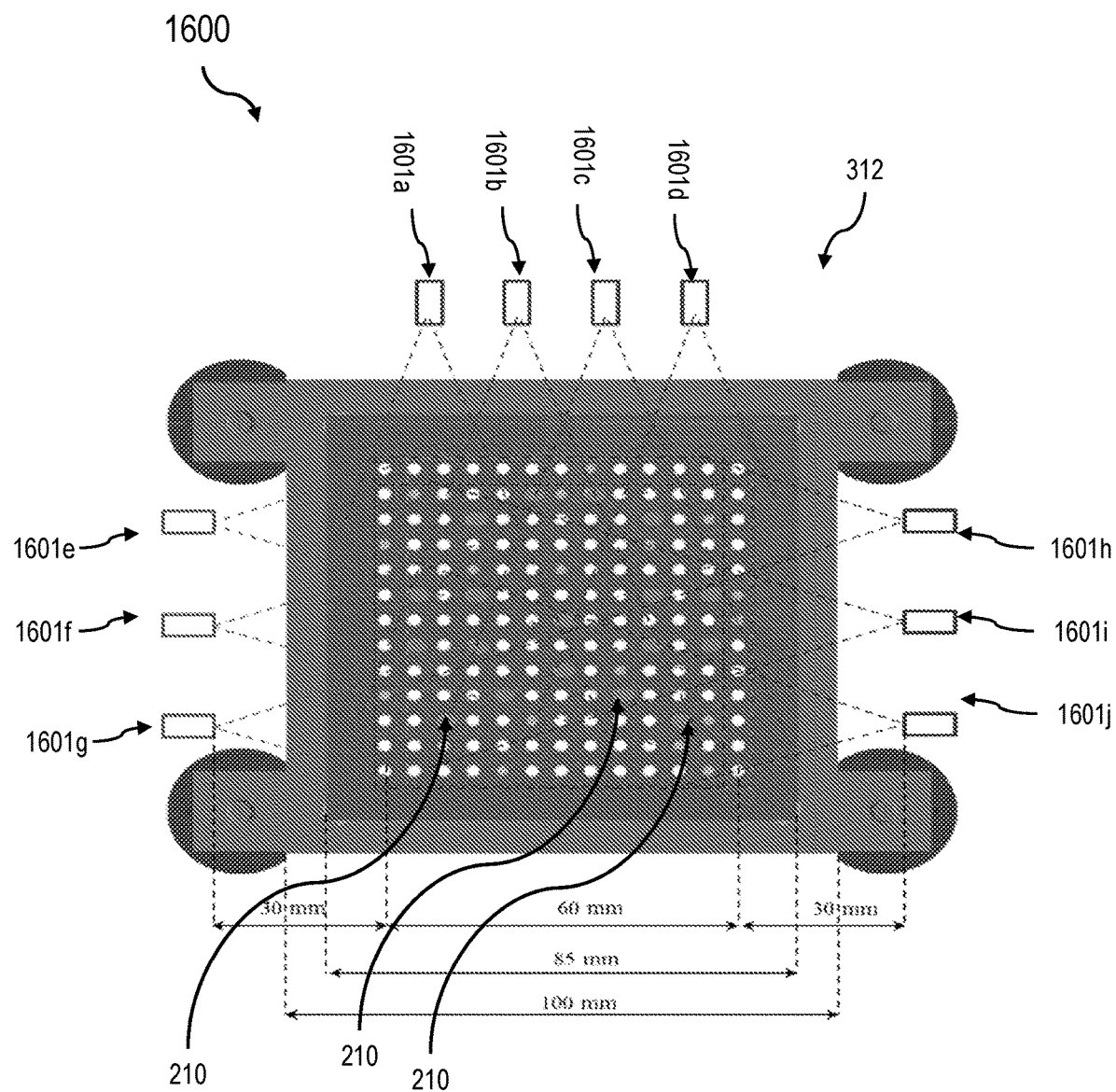
FIG. 16 is a schematic representation of camera placements with fields of view and coverage according to an aspect of the present invention.

In an aspect, the accuracy of radiation dose delivery with the RSBT system 100 depends on the precise positioning of the catheters 210. The catheter angles are simultaneously incremented throughout the treatment and can be displaced in depth due to needle position shifts that usually occur upstream after needle placement. In an aspect, the catheter position verification and correction system 700 can utilize a sensor system 1600 to control the placement for catheter depth and angular positions within the needles 350. In an aspect, the sensor system 1600, as shown in FIG. 16, captures feedback from individual sensors 1601a-j to verify that the catheter angular positions and depths are within an appropriate tolerance level for safe radiation delivery can be used in certain embodiments, discussed in more detail below.

Deviations in the angular positions and depths of RSBT catheters 210 need to be managed and corrected. The mechanical system (e.g., the combination afterloader 600 and multi-source RSBT apparatus 300) that rotates the catheters 210 consists of different components as shown in FIG. 3a. Any error associated with the manufacturing of these components, variation in friction between the catheters 210 and the apertures in the templates 310, 311, 312, error in the motor signals driving the moving template 312, unintended rotation of the template 312 as well as any backlash error associated with the system 100 can translate to deviations in catheter positions away from the desired positions. Embodiments of the catheter position verification and correction system 700 are designed to keep these deviations within a desired tolerance range for the treatment to be acceptable for clinical use while maintaining the uncertainty associated with the dose distribution at an appropriate level.

As described above, the mechanical system 600, and more specifically the multi-source RSBT apparatus 300, consists of two rigid templates 310, 311 with a moving template 312 in between. The moving template 312 converts translational motion into rotational motion of the rotating shafts 352. The rotating shafts 352 then rotate the connectors 351, which rotate the catheters 210 inside the needles 350. The lead screws 315 used to translate the moving template 312 are driven by motors (e.g., as a Maxon motor (Ø25 mm)). In an aspect of the present invention, it is beneficial to monitor the position of the catheters 210 based upon their rotation and relation to the moving template 312.

In an aspect, the monitoring of the position of the catheters 210 can be based upon the pitch of the rotating shaft 352, as well as change in position of the moving template 312, as discussed in more detail below. The pitch of the rotating shaft 352, $p_s$, is defined as the translation per unit rotation angle in degrees (e.g., 100 mm/360°=0.278 mm/°). The catheter 210 position $\Phi_m$ at any given time t can be determined by the template position of the moving template 312 $z_w(t)$, the deviation in template position $\Delta z_w(t)$, the shaft pitch $p_s$ and any inherent offset in the angular position of catheter m, $\Phi_m^0$, using the following equation:

$$\Phi_{m,w}(t) = \frac{z_w(t)}{p_s} + \frac{\Delta z_w(t)}{p_s} + \Phi_m^0 \qquad \text{(Eq. 1)}$$

where m is the catheter index and w is treatment position index, both of which can be represented as integers. If M is the total number of catheters 210, then m=1, 2 . . . , M Similarly, the pitch of the motor 301, $p_{mot}$, is defined as the number of motor revolutions per unit template translation in mm. $p_{mot}$ is calculated using the desired distance covered by the moving template 312 in a given amount of time and the rated speed of the selected motor 301 based on the recommended operating range and loading conditions for the motor 301.

For example, if the rated speed of the motor 301 is 7500 rpm (125 rps) and the moving template 312 moves 50 mm in 1 second, then $p_{mot}$ can be calculated as 125 revolutions/50 mm=2.5 revolutions/mm. The time (in seconds), $T_w$, for which the motor 301 needs to be on to move the template by a distance of $z_w$ mm using a motor 301 with a rated speed of 125 rps, can be determined using the following equation:

$$T_w = z_w \text{ (mm)} \cdot p_{mot}\left(\frac{\text{revolutions}}{\text{mm}}\right) \cdot \frac{1 \text{ (sec)}}{125 \text{ (revolutions)}} \qquad \text{(Eq. 2)}$$

Figure 9:
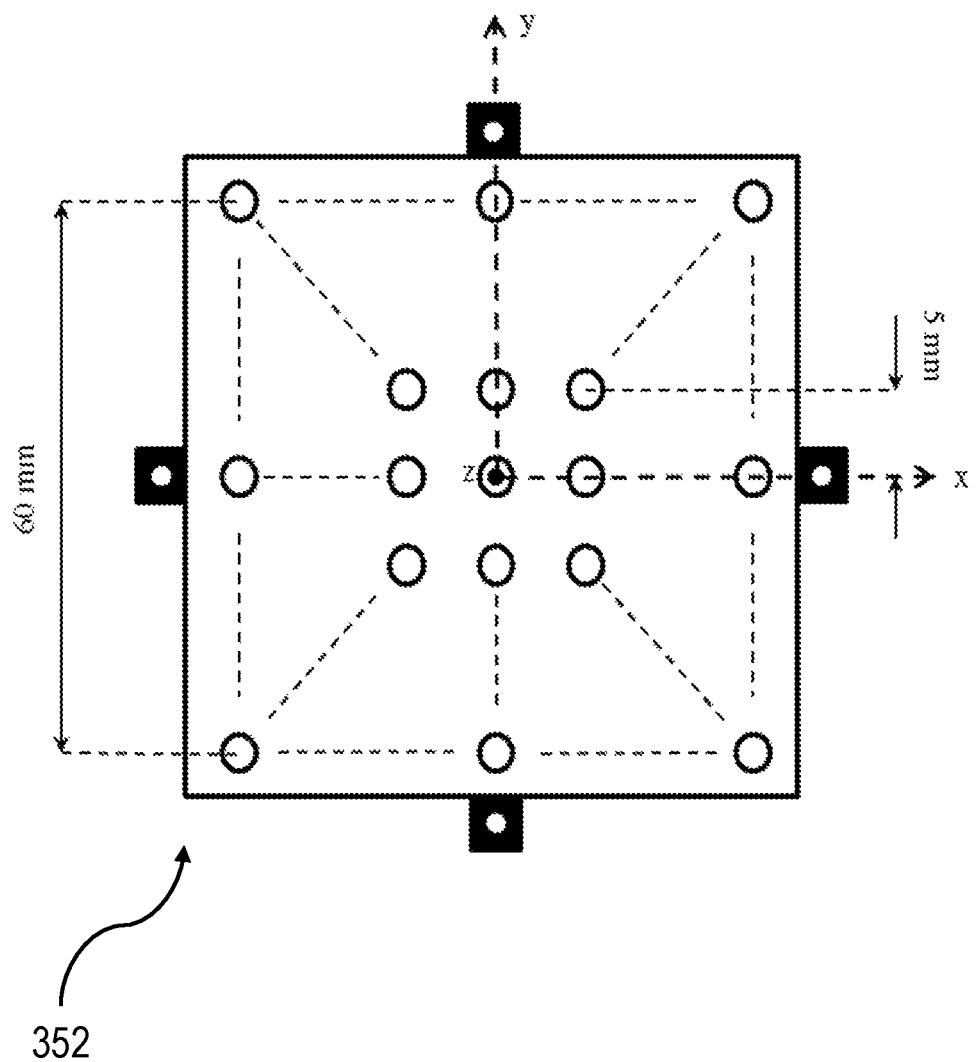
FIG. 9 is an illustration of a template geometry according to an aspect of the present invention.
Figure 10:
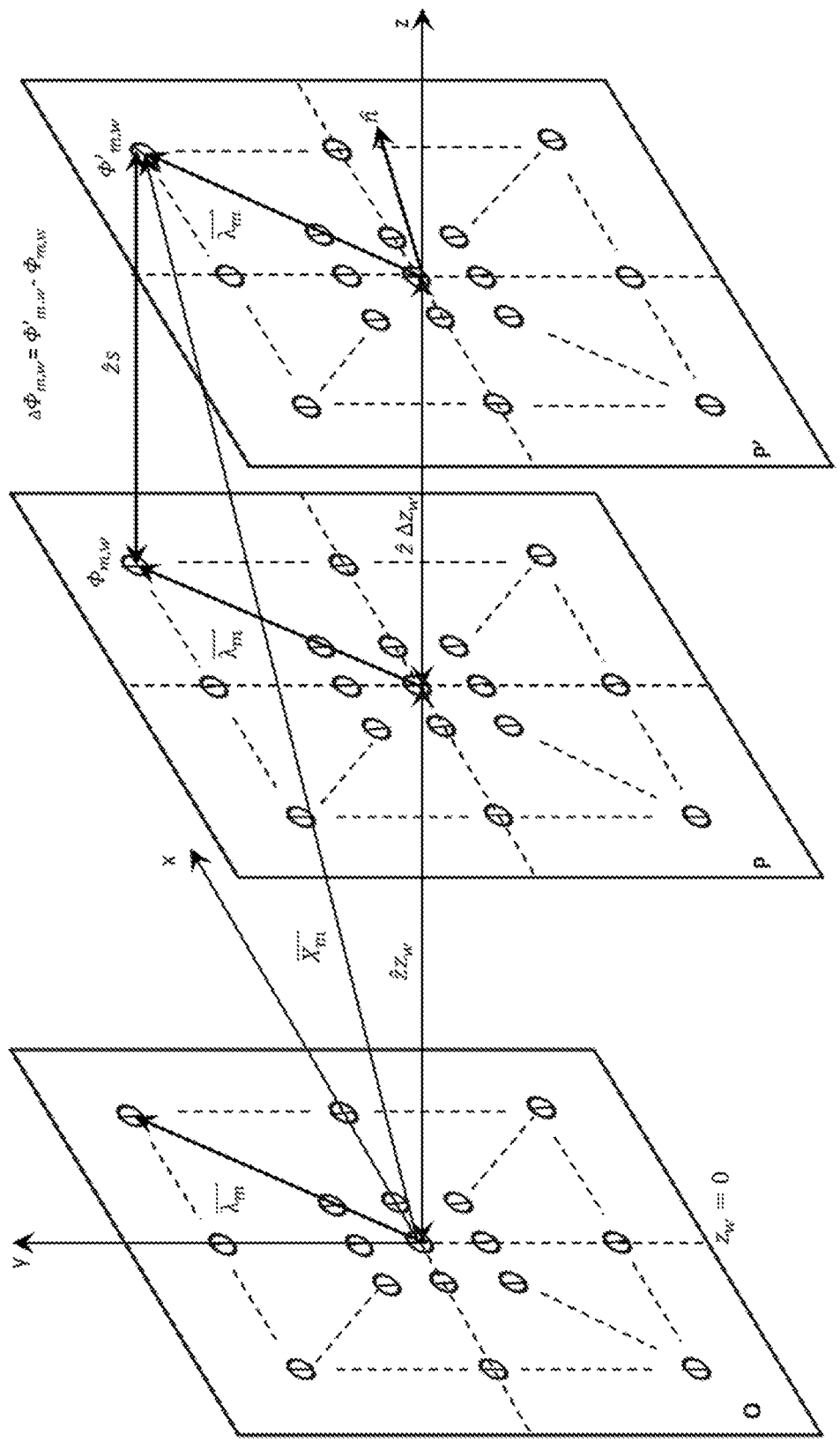
FIG. 10 is an illustration of a template geometry and a mathematical description for the center of each hole according to an aspect of the present invention.

FIG. 9 illustrates moving template geometry and dimensions according to an aspect of the present invention. As shown, the moving template dimensions are oriented along an x,y,z geometry, with the x and y direction aligned with the height and width of the template 312, and the z direction coming out of the front of the template geometry. FIG. 10 depicts the deviation in the moving template at each hole in the template due to a systematic template offset.

As discussed above, the moving template 312 contains a grid of apertures (13×13=169, for example, but not shown) for the rotating shafts 352 with spacing between adjacent apertures (5 mm separation, for example, as shown in FIG. 9). As discussed above, the ideal template position and orientation are determined using feedback from the sensors 1601a-j (see FIG. 16) and optimization to account for any deviations in the system and bring the catheters 210 to the desired angular orientations.

As shown FIG. 10, $\hat{z}$ is the unit vector along the template travel direction z, is the template orientation vector, which is a unit vector perpendicular to the template plane, $z_w$=0 is the initial position of the moving template origin (center of the template surface O), $z_w$ is the desired location of the moving template origin (surface P) relative to the initial position, $\Delta z_w$ is the deviation in the position of the template origin so that $(z_w+\Delta z_w)$ is the actual location of the moving template origin (surface P') relative to the initial position, $\Phi_{m,w}$ is the desired angle of catheter m, $\Phi'_{m,w}$ is the actual angle of catheter m, $\Delta\Phi_{m,w}$ is the difference between the actual and desired angles of catheter m, $\overrightarrow{\lambda_m}$ is the vector from the template origin to the center of hole m, s is the distance between the desired and actual center of hole m, and $\overrightarrow{X_m}$ is the vector from the template initial position origin to the actual location of the center of hole m. Other errors that can be introduced into the system are catheter backlash, manufacturing error in the catheters 210 and the moving templates 312 as well as error in the moving template orientation. The moving template 312 ideally moves along the z direction with the plane of the template perpendicular to the z axis. If the template is rotated about the x or y or both axes, then an orientation error is introduced in the system. From FIG. 10, $$\vec{X_m} = \hat{z}z_w + \vec{\lambda_m} + \hat{z}s \therefore \vec{X_m} \in P' \text{ if} \quad \text{(Eq. 3)}$$

$$[\vec{X_m} - \hat{z}(z_w + \Delta z_w)] \cdot \hat{n} =$$

$$\emptyset \Rightarrow (\hat{z}z_w + \vec{\lambda_m} + \hat{z}s) \cdot \hat{n} = \hat{z} \cdot \hat{n}(z_w + \Delta z_w) \Rightarrow$$

$$(\hat{z} \cdot \hat{n})z_w + \vec{\lambda_m} \cdot \hat{n} + s(\hat{z} \cdot \hat{n}) = (\hat{z} \cdot \hat{n})z_w + (\hat{z} \cdot \hat{n})\Delta z_w \Rightarrow s =$$

$$\frac{(\hat{z} \cdot \hat{n})\Delta z_w - \vec{\lambda_m} \cdot \hat{n}}{\hat{z} \cdot \hat{n}} = \Delta z_w - \frac{\vec{\lambda_m} \cdot \hat{n}}{\hat{z} \cdot \hat{n}} \text{ Also, } s = \Delta \Phi_{m,w} \cdot p_s$$

Figure 11:
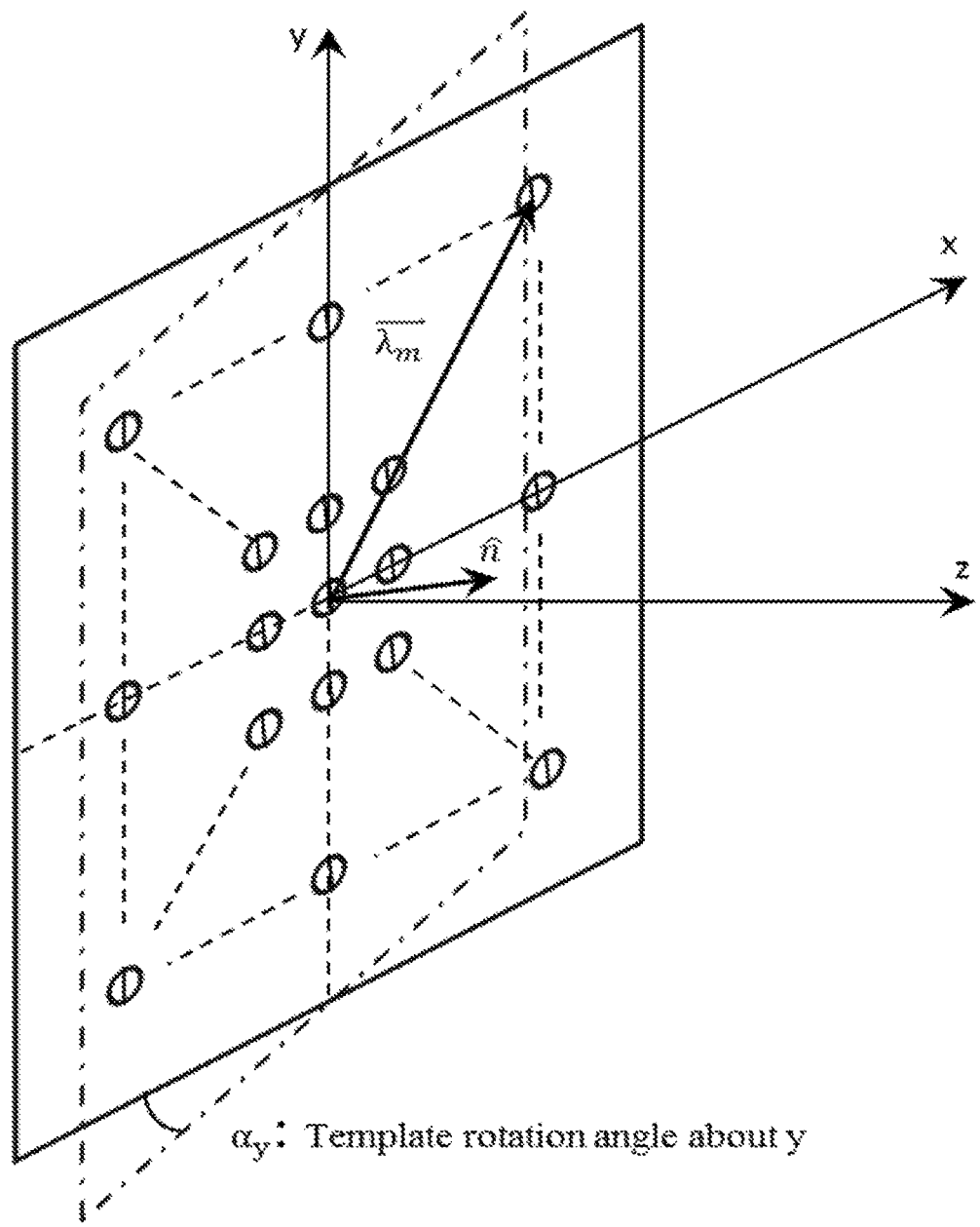
FIG. 11 is an illustration of a template orientation according to an aspect of the present invention.

The systematic deviation in catheter positions, $E_w$, to be minimized by optimization is given by:

$$E_w = \sum_{m=1}^{M} \left[\Delta \Phi_{m,w} \cdot p_s - \left(\Delta z_w - \frac{\vec{\lambda_m} \cdot \hat{n}}{\hat{z} \cdot \hat{n}}\right)\right]^2, \quad \text{(Eq. 4)}$$

where $\Delta z_w$ and $\hat{n}$ are the design variables of the optimization problem which are solved for and used along with backlash compensation to calculate the new position for the moving template 312 and minimize the deviations in catheter positions. FIG. 11 shows the misalignment of n with the z-axis caused by a deviation in the template orientation.

Based on the template dimensions (60 mm square, for example), $\vec{\lambda_m}$ for FIG. 11 can be calculated as follows:

$$\vec{\lambda_m} = \left(\frac{60}{2}\right)\cos\alpha_y \hat{x} + \left(\frac{60}{2}\right)\hat{y} + \left(-\frac{60}{2}\right)\sin\alpha_y \hat{k} \quad \text{(Eq. 5)}$$

The optimization problem can be defined as follows:

$$\text{Minimize } E_w = \sum_{m=1}^{M} \left[\Delta \Phi_{m,w} \cdot p_s - \left(\Delta z_w - \frac{\vec{\lambda_m} \cdot \hat{n}}{\hat{z} \cdot \hat{n}}\right)\right]^2 \quad \text{(Eq. 6)}$$

$$ST: \Delta z_l \leq \Delta z_w \leq \Delta z_u$$

$$n_x^2 + n_y^2 + n_z^2 = 1 - \sin\alpha_{y_{max}} \leq n_x \leq$$

$$\sin\alpha_{y_{max}} - \sin\alpha_{x_{max}} \leq n_y \leq \sin\alpha_{x_{max}} \cos\alpha_{y_{max}} \leq n_z \leq 1$$

where $\Delta z_w$, $n_x$, $n_y$, and $n_z$ are the variables, M is the number of catheters 210 (20, for example), m is the catheter index, w is the treatment position index (10 treatment positions, for example), $\Delta z_u$ and $\Delta z_l$ are the upper and lower bounds on the translational deviation of the moving template (±5 mm, for example) and $\alpha_{x_{max}}$ and $\alpha_{y_{max}}$ are the maximum possible template rotation about x and y axes respectively (±5°, for example).

Optimization of the template position is continuously performed throughout the RSBT delivery process. Other objective functions could also be used in the formulation. Once optimal $\Delta z_w$ and $\hat{n}$ values are determined, motor signals are generated to correct deviations in the template position using the above optimization equations. A positive $\Delta z_w$ implies that the moving template 312 is ahead of the desired position and needs to be moved in the reverse direction to apply the correction. Similarly, for a negative $\Delta z_w$, the template 312 is moved in the forward direction to apply the correction. Optimal $n_x$, $n_y$ and $n_z$ values are then used to determine the orientation deviation of the template 312 about the x and/or y axis and the corresponding longitudinal deviation. The direction of template motion while correcting for deviation in the template position, is maintained when correcting for the template orientation error in order to avoid backlash issues.

Figure 12:
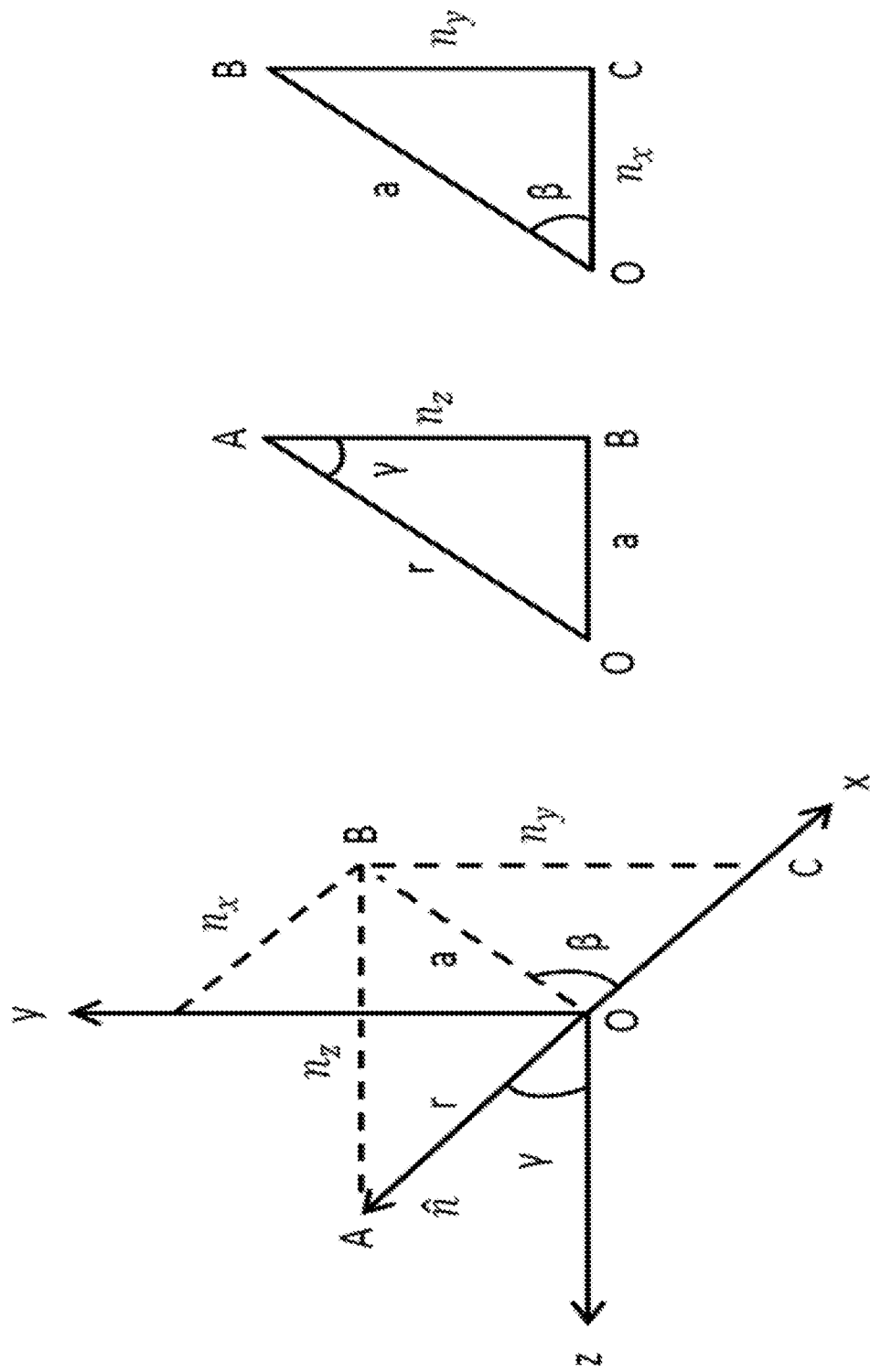
FIG. 12 is an illustration of a conversion from a rectangular to a spherical coordinate system for n definition according to an aspect of the present invention.

An alternate representation of the objective function in Eq. 6 is obtained by converting the rectangular coordinates of the orientation vector $\hat{n}$, namely $n_x$, $n_y$ and $n_z$ into spherical coordinates $\gamma$ and $\beta$ as shown in FIG. 12. The zenith angle, $\gamma$, is defined as the angle between the zenith direction z and $\hat{n}$. The azimuthal angle, $\beta$, is defined as the angle between the x axis and the orthogonal projection OB of $\hat{n}$ on the x-y plane. From FIG. 12, triangles OAB and OBC give us:

$$\alpha = \sin\gamma$$

$$n_z = \cos\gamma \quad n_x = \alpha \cos\beta = \sin\gamma \cos\beta$$

$$n_y = \alpha \sin\beta = \sin\gamma \sin\beta \quad \text{(Eq. 7)}$$

Expanding the deviation term, $E_w$ and using substitution, one obtains:

$$E_w = \sum_{m=1}^{M} \left[\Delta \Phi_{m,w} \cdot p_s - \left(\Delta z_w - \frac{\vec{\lambda_m} \cdot \hat{n}}{\hat{z} \cdot \hat{n}}\right)\right]^2$$

$$= \sum_{m=1}^{M} \left[\Delta \Phi_{m,w} \cdot p - \left(\Delta z_w - \frac{\lambda_n n_x + \lambda_y n_y + \lambda_z n_z}{n_z}\right)\right]^2$$

Since $\lambda_z = 0$, we obtain:

$$E_w = \sum_{m=1}^{M} \left[\Delta \Phi_{m,w} \cdot p - \left(\Delta z_w - \left(\lambda_x \frac{n_x}{n_z} + \lambda_y \frac{n_y}{n_z}\right)\right)\right]^2$$

$$= \sum_{m=1}^{M} [\Delta \Phi_{m,w} \cdot p - (\Delta z_w - (\lambda_x \tan\gamma\cos\beta + \lambda_y \tan\gamma\sin\beta))]^2.$$

The constraints become:

$$\Delta z_l \leq \Delta z_w \leq \Delta z_u$$

$$\gamma_{min} \leq \gamma \leq \gamma_{max}$$

$$0 \leq \beta \leq 2\pi \quad \text{(Eq. 8)}$$

where $\gamma_{min}$ and $\gamma_{max}$ define the range of angles to which y is restricted to (±5° for example).

Simultaneously controlling the rotation angle of multiple catheters inside a patient is a complex problem in which accounting for catheter backlash is of fundamental importance.

Figures 13A, 13B:
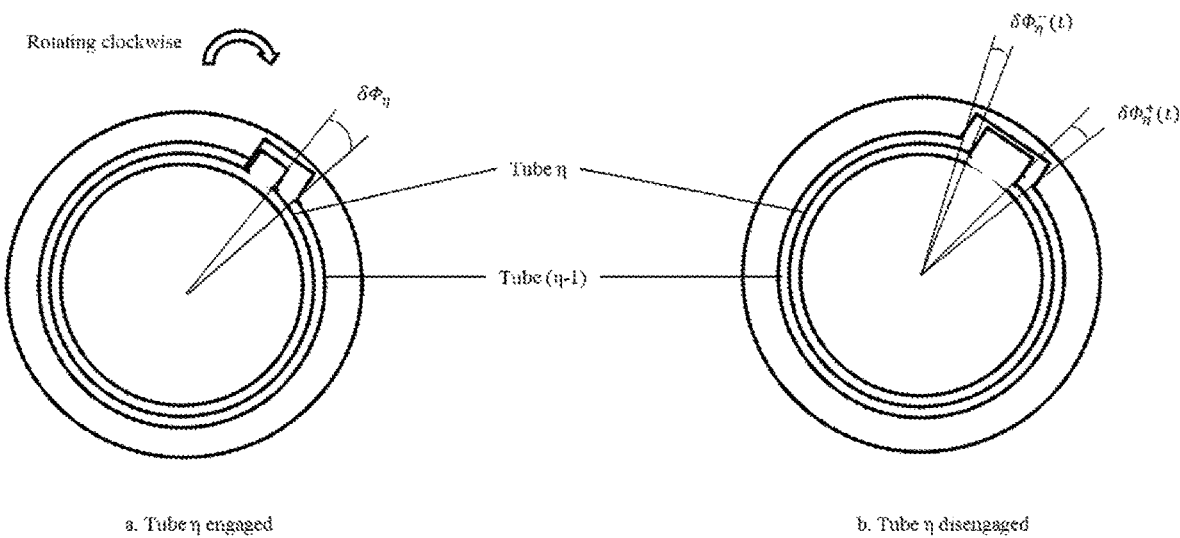
FIGS. 13a-b illustrate backlash according to an aspect of the present invention.

At any given moment in time, all the RSBT delivery devices 200 and the delivery system 300, namely, the shaft 352, the connector 351 and the catheter 210 are either in an "engaged" or a "disengaged" state as shown in FIG. 13a and FIG. 13b. If the rotating shaft 352 is tube η, then the connector 351 is its neighboring tube η−1. If tube η is in a disengaged state, then it rotate by δΦ⁻ in the negative direction or $\delta\Phi^+$ in the positive direction in order to become engaged. If tube $\eta$ is in the engaged state with its neighboring control tube $\eta-1$, then tube $\eta$ becomes disengaged with tube $\eta-1$ if tube $\eta$ changes rotational directions. Tube $\eta-1$ remains engaged if tube tube $\eta$ stops or continues to rotate in the same direction. Tubes can only be engaged with their neighbors. The angular position of the tube indexed by $\eta$, $\Phi_\eta$, is given by:

$$\Phi_\eta(t) = \int_0^t \omega_\eta(t')dt' + \Phi_\eta^0 \qquad \text{(Eq. 9)}$$

where $\omega_\eta$ is the angular velocity of tube $\eta$ and $\Phi_\eta^0$ is any inherent offset in the angular position of tube $\eta$. If tube $\eta$ is engaged with tube $\eta-1$ at time t, then angular positions and angular velocities match, therefore:

$$\omega_\eta(t) = \omega_{\eta-1}(t) \text{ and } \Phi_\eta(t) = \Phi_{\eta-1}(t) \qquad \text{(Eq. 10)}$$

Let $\delta\Phi_\eta$ be the angular backlash between tubes $\eta$ and $\eta-1$. Rotating tube $\eta-1$ by angle $\delta\Phi_\eta$ guarantees that tubes $\eta-1$ and $\eta$ will be engaged. It is thus guaranteed that tube $\eta$ will be engaged if tube 0 is rotated by $\delta\Phi_1 + \ldots + \delta\Phi_\eta$. Suppose tube $\eta$ is engaged with tube $\eta-1$ and tube $\eta-1$ undergoes a change in the angular velocity direction at time $t_c$. Then $\omega_\eta(t_c)=0$, and $$\delta\Phi_\eta^-(t) = \int_{t_c}^t dt' \omega_{\eta-1}(t') = \Phi_{\eta-1}(t) - \Phi_{\eta-1}(t_c), \qquad \text{(Eq. 11)}$$

$$\text{and } \delta\Phi_\eta^+(t) = \delta\Phi_\eta - \delta\Phi_\eta^-(t).$$

If $\delta\Phi_\eta^-(t)<0$, then the angular velocity direction is reversed again, is in the same direction as it was when tubes $\eta-1$ and $\eta$ were last engaged, and Eq. 10 applies. If $\delta\Phi_\eta^+(t)>0$, then tube $\eta-1$ has traveled a net angle of $\delta\Phi_\eta$ since disengaging from tube overcoming the backlash, and resulting in Eq. 10 applying again.

The following simulation of a single catheter system shows the importance of accounting for catheter backlash and compensating for it with regards to the time and accuracy of the treatment. The parameters used for the simulation are:

Desired catheter position $\Phi_1 = 20°$ (Eq. 12)

Shaft pitch $p_s = 100$ mm/360 deg = 0.278 mm/deg $\therefore$ Desired template position $z_1 = \Phi_1 \cdot p_s = 5.56$ mm Motor pitch $p_{mot} = 125$ rev/50 mm = 2.5 rev/mm $\therefore$ motor ON time $T_w =$ $$z_1 \text{mm} \cdot p_{mot} \frac{\text{rev}}{\text{mm}} \cdot \frac{1 \text{ sec}}{125 \text{ rev}} = 0.1112 \text{ sec}$$

Manufacturing error = 4°

Total backlash = $\delta\Phi_1 + \ldots + \delta\Phi_\eta = 10°$.

Figure 14:
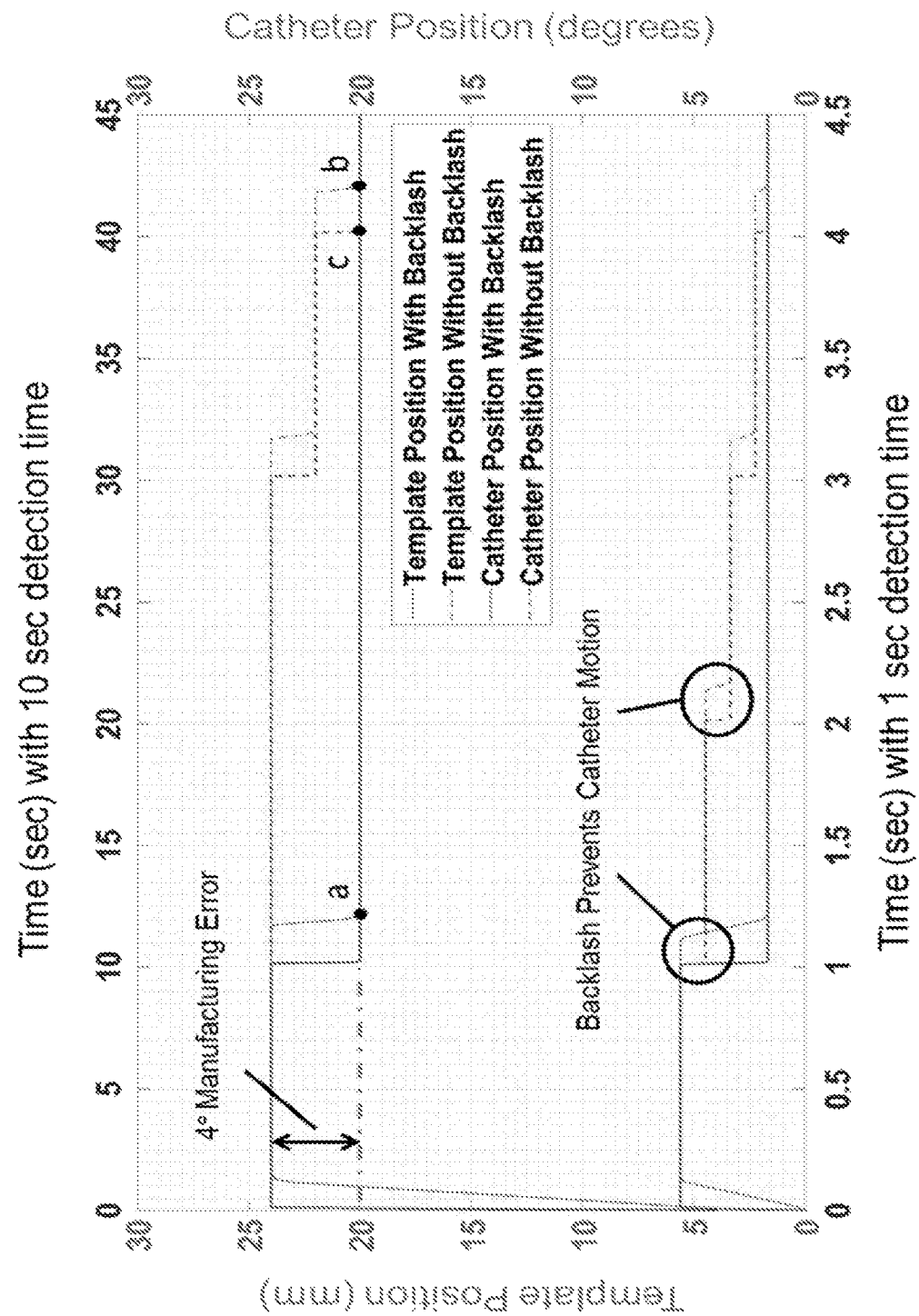
FIG. 14 is an illustration of catheter and template positions with and without backlash compensation for 1 sec and 10 sec detection times, according to an aspect of the present invention.

The total time taken by the catheter position verification and correction system 700 to detect the actual angular position of the catheter 210, calculate the deviation in the position, run optimization to determine the optimal $\Delta z_w$ and orientation $\hat{n}$ values and generate motor signals to correct the deviation, is termed as detection time, $T_d$. FIG. 14 shows a comparison of systems correcting for deviation in the catheter position with and without backlash compensation. The figure also shows the enhanced effect of backlash on a system with a slower $T_d$.

For example, a system with backlash compensation and $T_d=1$ second takes 1.3 seconds (point a) to bring the catheter 210 to the desired position of 20°. The same system without backlash compensation takes 4.3 seconds (point b). Similarly, a system without backlash compensation and $T_d=10$ seconds takes 40.5 seconds (point c) to bring the catheter 210 to the desired position which is a 10-fold increase in time taken to correct for any deviations. So accounting and compensating for catheter backlash in feedback is of fundamental importance to reduce treatment times especially for a system that does not detect catheter positions instantaneously and accurately.

Figure 15:
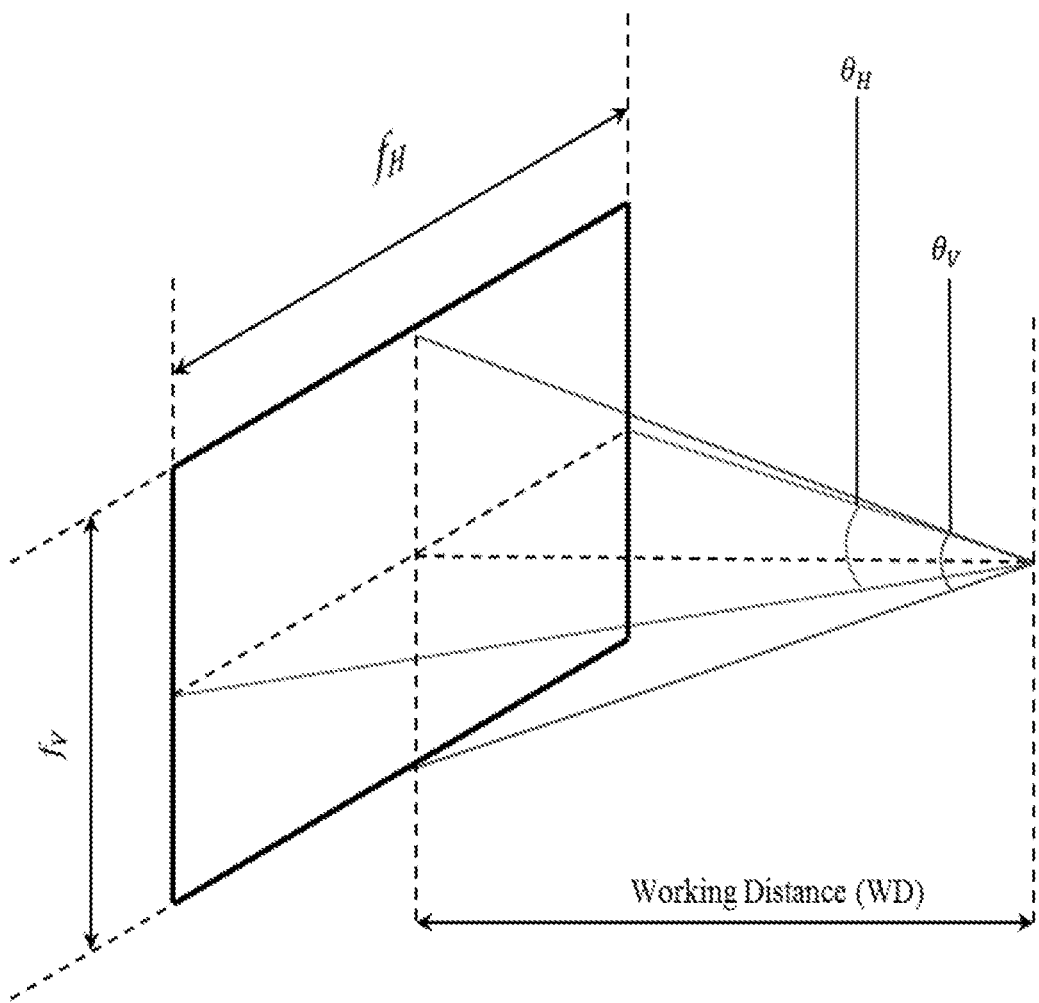
FIG. 15 illustrates fields of view according to an aspect of the present invention.

As discussed above, the catheter position verification and correction system 700 can utilize a sensor system 1600, shown in FIG. 16. In an aspect, the sensor system 1600 includes a plurality of sensors 1601. Optical sensors 1601 can be utilized. For example, sensors 1601 can include aMD-B5014V, 5 megapixel, UVC QSXGA camera modules from MISUMI Electronic Corporation. However, other sensor types can be used, including, but not limited to, Raspberry Pi camera modules and Varioptic Liquid Lenses. As shown, optical sensors 1601a-j are placed along the sides of the apparatus at the distal end of the angular drive mechanism, attached to the fixed template 311. For a camera module with horizontal image sensor size h, vertical image sensor size v, focal length f and a working distance WD, the horizontal field of view ($f_H$), the vertical field of view ($f_V$) and the angular field of view ($\theta$) describe the inspection area captured on the image sensor. $f_H$, $f_V$ and $\theta$ are depicted in FIG. 15 and calculated using the following equations:

$$f_H = h \cdot WD/f$$

$$f_V = v \cdot WD/f$$

$$\theta_H = 2 \cdot \arctan(h/(2f))$$

$$\theta_V = 2 \cdot \arctan(v/(2f)) \qquad \text{(Eq. 13)}$$

As discussed above, a MD-B5014V camera module 1601 can be used. The MD-B5014V camera module 1601 has an image sensor of 2.592 mm (h)×1.944 mm (v) and a focal length (f) of 3.87 mm. It is an auto-focus camera 1601 with a focusing distance range of 35 mm to infinity. For the given h, v and f values and an assumed working distance of 30 mm, the camera has an $f_H$ of 20 mm, $f_V$ of 15 mm, $\theta_H$ of 37 degrees and $\theta_V$ of 28 degrees.

Figure 17:
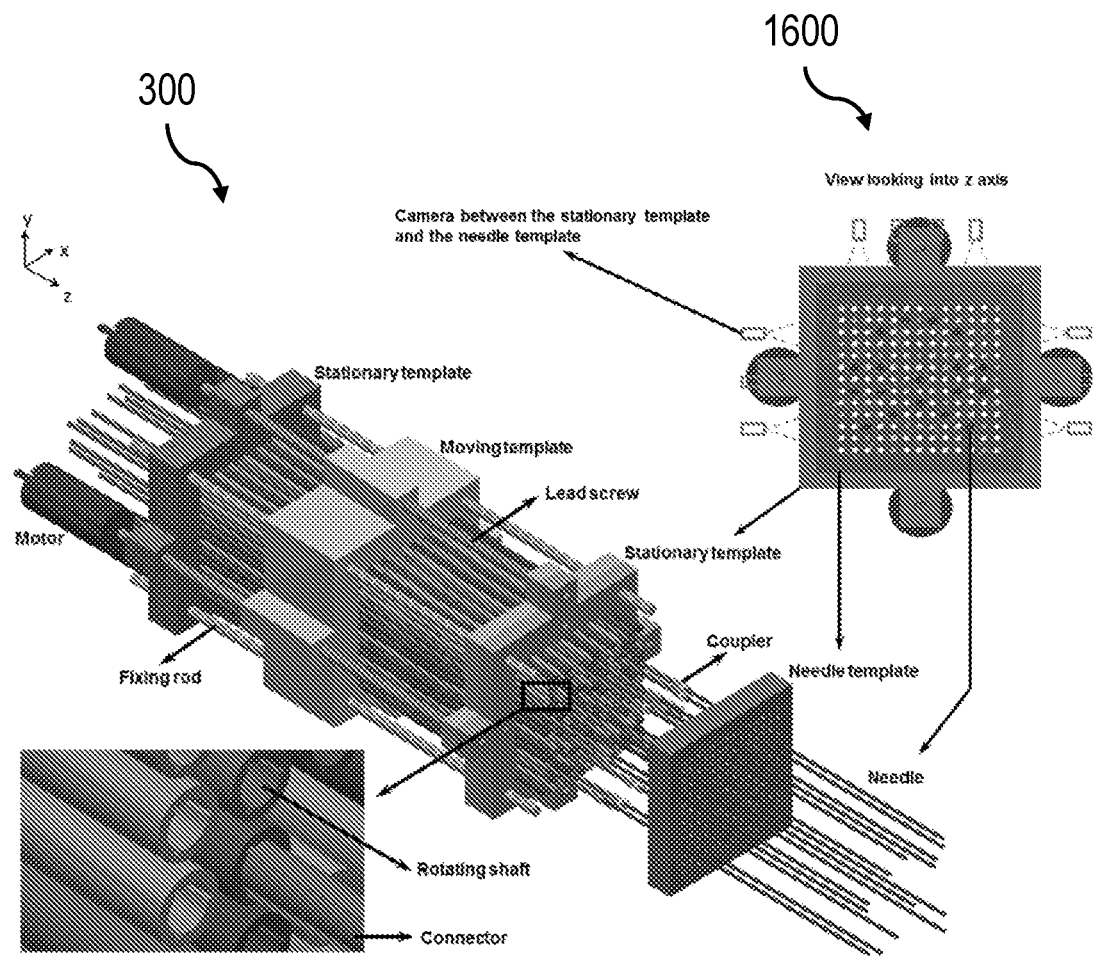
FIG. 17 is an illustration of the sensor placement relative to the RSBT angular drive system, according to an aspect of the present invention.

FIG. 16 depicts an arrangement 1600 of ten sensors 1601a-j (in this case, camera modules) with respect to the template 312 along with the fields of view and coverage based on values described above. The solid filed in portions within the apertures of the template show a catheter configuration used by White et al for high dose rate brachytherapy (HDR-BT). Based on the auto-focusing range of the camera 312, all the catheters 210 are visible from at least two cameras 160 and provide the desired redundancy except in cases where a particular configuration may lead to one or more catheters 210 being obscured by other catheters 210. To overcome this challenge, a covariance table is developed based on regression analysis to estimate the positions of catheters that are obscured from the camera system using the positions of catheters that are visible. FIG. 17 shows the placement of the sensors and template arrangement 1600 with respect to the RSBT angular drive mechanism 300.

Modeling of System

Figure 18A:
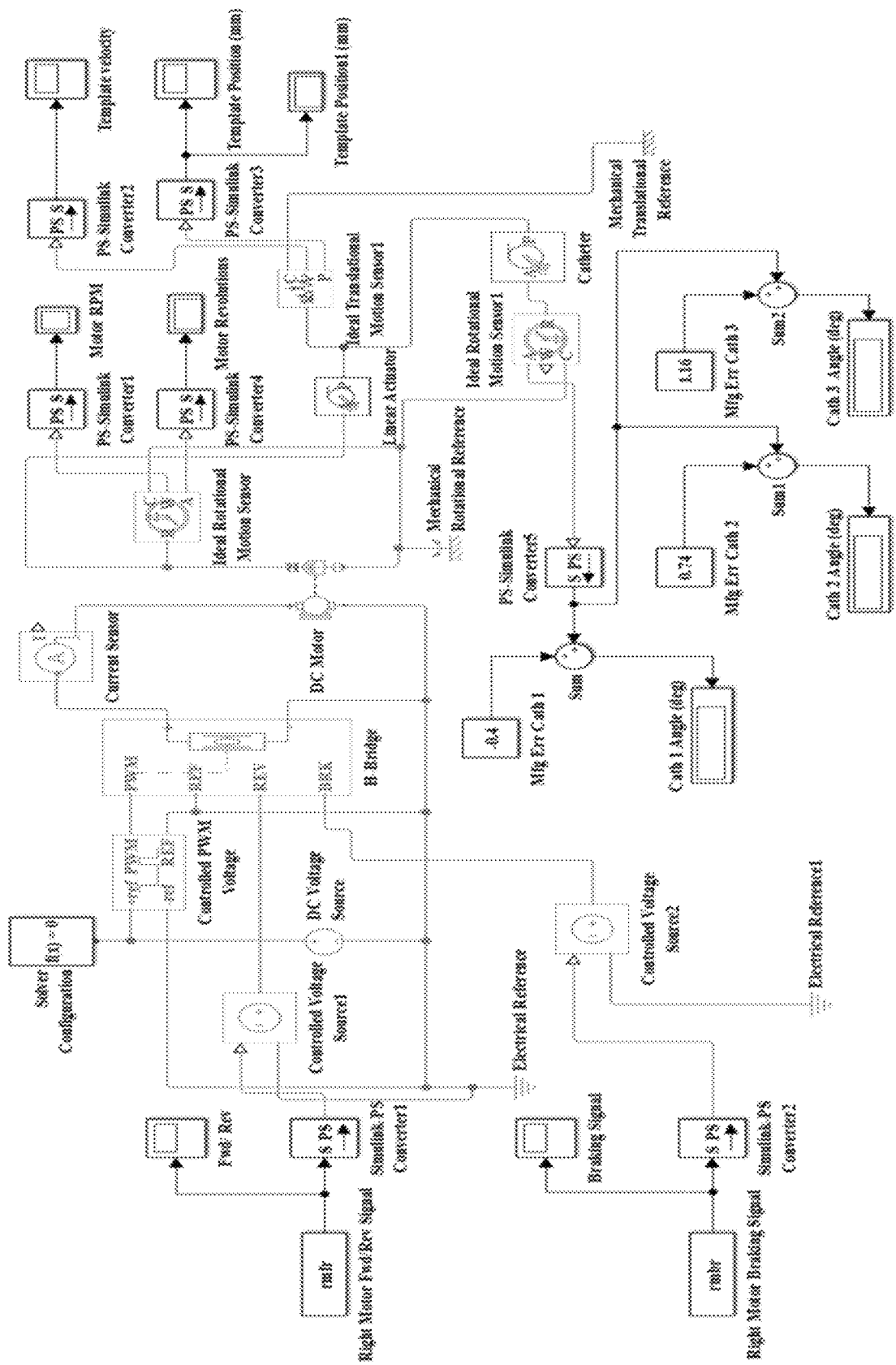
FIGS. 18a-b illustrate a simulation process, according to an aspect of the present invention.

In an aspect, the entire mechanical system (300 and 600) was simulated. The modeling consisted of a set of motors 302 driving lead screws 315 to control the moving template 312. The model is shown in FIG. 18a. An H Bridge is used to control motor ON-OFF and the direction of rotation (FWD/REV). The model consists of a wheel and axle assembly denoted as 'Linear Actuator' that depicted the conversion of the rotary motion of the lead screws to the linear motion of the template. Another wheel and axle assembly denoted as 'Catheter' depicted the conversion of the linear motion of the template to the corresponding rotary motion of the catheters. Motor signals were generated in MATLAB based on the required motor ON/OFF time, direction of rotation and template movement to get the catheters in the desired treatment positions. The actual catheter positions were fed back to calculate any deviations ($\Delta\Phi$) in them, depicting the camera monitoring system in the physical set up.

Figure 18B:
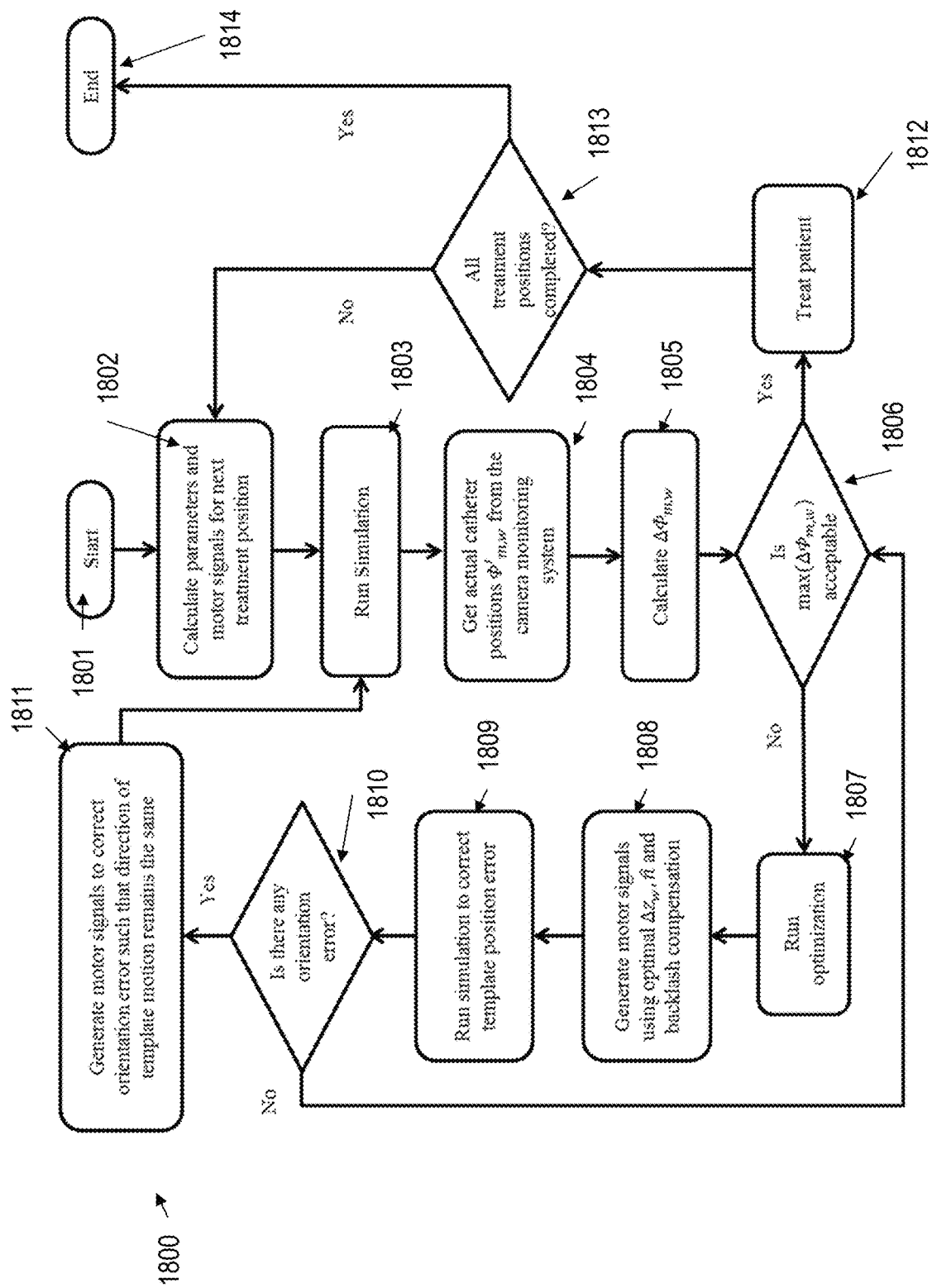

A process flow 1800 for adjusting positions and treating patients is shown in FIG. 18b. In step 1801, the process starts. In step 1802, the system calculates parameters and motor signals for the next treatment position. In step 1803, the simulation described above is run. In step 1804, the actual catheter position is received from the sensors. These actual catheter positions are fed back to calculate any deviations ($\Delta\Phi$) in them. This feedback depicts the camera monitoring system in the physical set up, and in step 1805, $\Delta\Phi$ is calculated. In step 1806, if the $\Delta\Phi$ is in the acceptable range, then treatment is provided to the patient in step 1812. If all treatments are completed in step 1813, then the process ends in step 1814. Otherwise, motor signals are calculated to move the catheters to the next treatment position in step 1802.

In step 1806, if $\Delta\Phi$ is not in the acceptable range, then the optimization problem is solved in step 1807 to determine the optimal change in template position ($\Delta z_w$) and orientation ($\hat{n}$) to minimize the deviations in catheter positions. These optimal values of $\Delta z_w$ and $\hat{n}$ along with backlash compensation (if required) are used to calculate the new template position and generate corresponding motor signals to move the template in step 1808. In step 1809, the simulation is run to correct template position errors. Step 1806-1810 can be repeated until there are no orientation errors to be removed in step 1810. In step 1811, the system generates motor signals to correct orientation error such that the direction of template motions remains the same.

Using the method discussed above, a nine catheter system was simulated which includes the eight outermost catheters and the one central catheter. Manufacturing error and template orientation error were introduced in the system. The manufacturing error used for this example is normally distributed with mean and standard deviation of 1° (N (1°, 1°)). Manufacturing error inherent in the system can be determined during the installation and commissioning process of the system and can be accounted for by the Treatment Planning System (TPS) before radiation delivery. The following parameters are used for the simulation:

$$\text{Desired catheter position } \Phi_{m,1} = 20° \quad (\text{Eq. 14})$$

$$\text{Shaft pitch } p_s = 100 \text{ mm}/360 \text{ deg} = 0.278 \text{ mm/deg}$$

$$\therefore \text{Desired template position } z_1 = \Phi_{m,1} \cdot p_s = 5.56 \text{ mm}$$

$$\text{Motor pitch } p_{mot} = 125 \text{ rev}/50 \text{ mm} = 2.5 \text{ rev/mm}$$

-continued $$\therefore \text{motor ON time } T_w = z_1 \text{mm} \cdot p_{mot} \frac{\text{rev}}{\text{mm}} \cdot \frac{1 \text{ sec}}{125 \text{ rev}} = 0.1112 \text{ sec}$$

$$\text{Manufacturing error} = [-0.4°, 0.74°, 1.16°, 1.75°, 0.72°, 2.57°, 0.52, 1.32°, 1.66°] \sim N(1°, 1°)$$

$$\text{Backlash error} = 10°$$

$$\text{Template orientation error} = 2 \text{ mm},$$

counter clockwise about vertical $y$ axis

Figure 19:
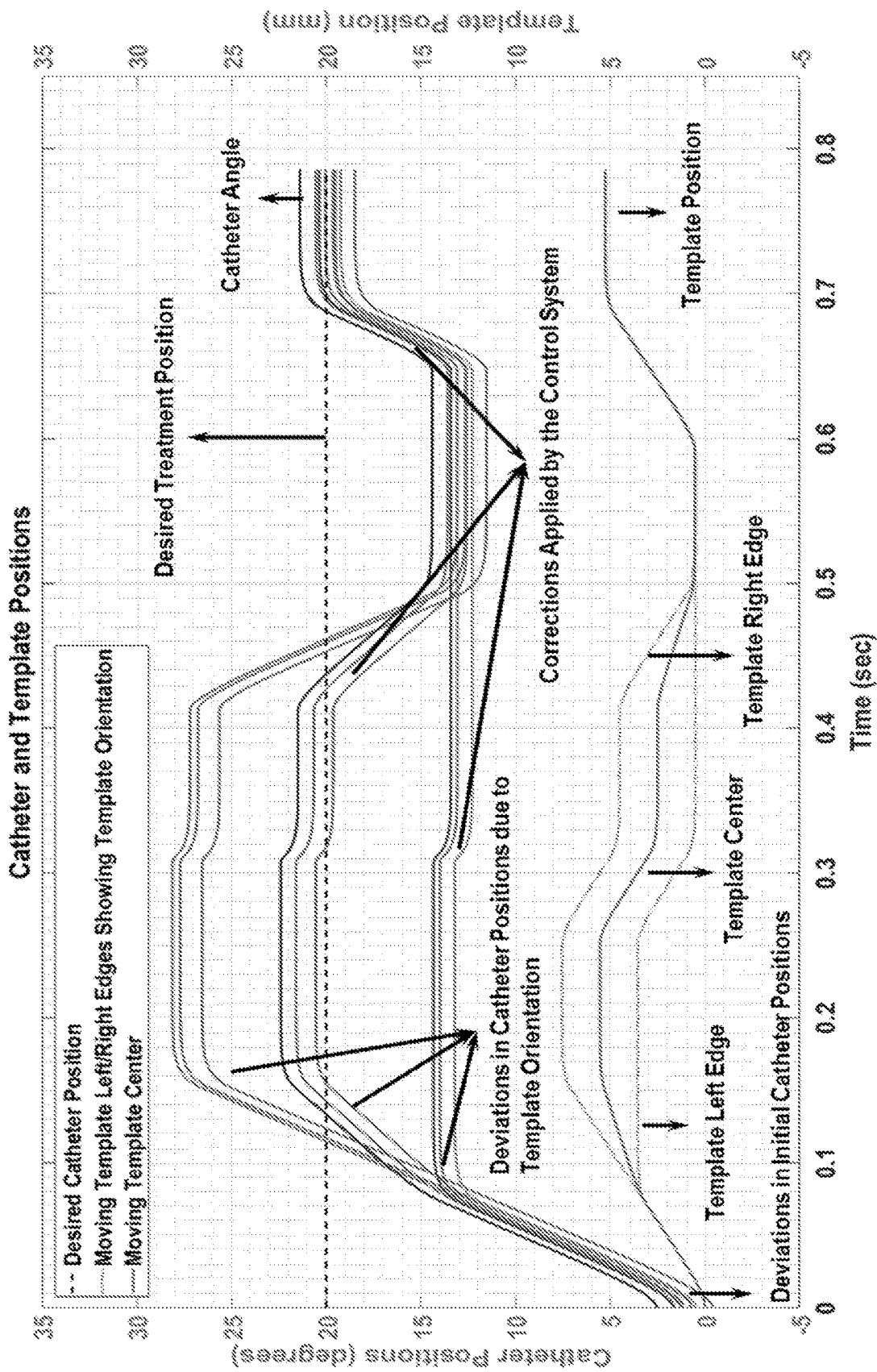
FIG. 19 is an illustration of catheter and template positions for 2 mm template orientation error with backlash compensation, according to an aspect of the present invention.
Figure 20:
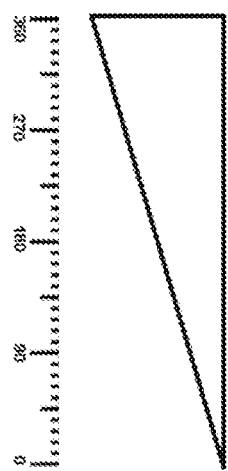
FIG. 20 is a right-triangle pattern with angular ruler according to an aspect of the present invention.

FIG. 19 shows how deviations in the positions of the nine catheters are minimized and brought within an acceptable range using optimization and feedback, according to an aspect. Following adjustment, the catheter positions are within ±1.5 degrees of the desired treatment position of 20 degrees which is denoted by the dashed line.

The template motion is shown at the bottom of the plot and the catheter positions are shown at the top. Due to orientation error in the system, the template motion plot has three different profiles that depict the three parts of the moving template, namely, the left side, the center and the right side of the template. The example incorporates manufacturing and orientation errors as well as their correction along with backlash compensation. The catheters are assumed to be in the engaged position to start with. As the template starts moving longitudinally, the catheters start rotating. From FIG. 19, an orientation error is introduced in the system at 0.15 seconds when one of the edges of the moving template moves ahead of the other edge. This translates to deviations in the catheter positions. An optimization problem is solved to determine the optimal change in template position ($\Delta z_w$) and orientation ($\hat{n}$) to minimize the deviations in catheter positions. It can be seen from FIG. 19 that the first correction is applied at 0.25 seconds where the template starts moving in the reverse direction. Since a change in the template motion direction is involved, backlash occurs in the correction process and needs to be accounted for. The template starts moving in the reverse direction at 0.25 seconds. The catheters, however, start rotating at 0.31 seconds only after the backlash is overcome. The system then checks for any deviations in the template orientation. Correction of template orientation is applied at 0.42 seconds. Since the direction of motion is still reverse, the catheters are already engaged and start rotating as the template starts moving. Catheter positions can be monitored by the sensors with high frequency (every 0.1 seconds using a camera with a frame rate of 10 frames per second (fps), for example). The catheter positions are especially monitored by the camera system after any template position and/or orientation corrections are applied. The optimization problem is solved again to obtain the optimal $\Delta z_w$ to correct for any deviations. The template position correction is fully applied at 0.59 seconds and the catheters are rotated to the desired angular positions.

Even with multiple camera modules monitoring the catheters, there is still a possibility that for a given catheter configuration, some catheters are obscured by other catheters. To overcome this challenge, regression analysis is used to generate a covariance table and estimate the positions of obscured catheters. From FIG. 10, deviation in catheter positions is described by $$\Delta\Phi_{m,w} = \Phi'_{m,w} - \Phi_w \quad (\text{Eq. 15})$$

A line of best fit for the deviations can be calculated using regression analysis to obtain coefficients $a_{m,m'}$ and $b_{m,m'}$. If $\overline{\Delta\Phi_m}$ is the known independent variable corresponding to the visible catheter position at index m and $\overline{\Delta\Phi_{m,m'}}$ is the dependent variable corresponding to the blocked catheter position at index m', then the blocked catheter positions can be estimated using the following equation:

$$\overline{\Delta\Phi_{m,m'}} = a_{m,m'}\overline{\Delta\Phi_m} + b_{m,m'} \qquad \text{(Eq. 16)}$$

The $a_{m,m'}$ coefficient represents the slope of the regression line which corresponds to how much the two variables change with respect to each other. Such a variation can be caused by any errors in the manufacturing of the mechanical components or variation in friction between the catheters and the holes in the templates of the mechanical system. Since the change in catheter positions is very similar for all catheters, we get $$a_{m,m'} \cong 1 \text{ for all m, m'} \qquad \text{(Eq. 17)}$$

The $b_{m,m'}$ coefficient represents the intercept of the regression line which corresponds to the blocked catheter position when the angle of the visible catheters is zero. For an n catheter system, regression analysis is used during the installation and commissioning process to output an n x n matrix of regression coefficients $b_{m,m'}$ with 0s along the diagonal for the case when m=m'. $b_{m,m'}$ is the offset added to the position of the visible catheter m to obtain the position of the obscured catheter m'. The method provides results for the deviations in the positions of the catheters that are not visible to the sensors 1601a-j with high accuracy.

In an aspect, the monitoring system consists of an angle-dependent pattern (a right-triangle pattern, for example) etched onto the walls of the catheter along with an array of sensors (cameras, for example) that captures images of this angular pattern. The pattern recognition software (based on Canny edge detection method, for example) processes these images to identify the angular pattern and determine the actual rotation angle of the catheters.

Prototype System

A prototype system was constructed to validate the simulation results. A right-triangle pattern of known base length, b, shown in FIG. 20, was etched onto the walls of the catheter. The etched-pattern also included an angular ruler next to the right-triangle to assist in identifying the true catheter rotation angle. The output from the pattern recognition software was compared with the value from the angular ruler to verify the effectiveness of the algorithm.

The MD-B5014V, 5 megapixel, UVC QSXGA camera module from MISUMI Electronic Corporation was used to image the catheters. The pattern recognition software was implemented in MATLAB and was based on the Canny method and polynomial curve fitting. The Canny edge detection method was initially used with a low threshold to determine majority of the edges, identify the catheter boundary and determine the center of the catheter. Although it provided detailed edges, the lower threshold also led to a lot of noisy edges. After the catheter center was determined, the Canny method was run again with a higher threshold to identify only the significant edges related to the triangle pattern and the angular ruler. A polynomial curve was fit to the left and right edges of the pattern boundary. The number of pixels, p, between the two sides adjacent to the base of the triangle along the catheter center was measured by the control system and converted to distance, d, using the resolution, r, of the image using the equation $$d_{m,w} = p_{m,w} * r. \qquad \text{(Eq. 18)}$$

The actual angular position of the catheter m for treatment position w is determined using the equation $$\Phi'_{m,w} = d_{m,w} * \frac{360}{b}. \qquad \text{(Eq. 19)}$$

Figure 21:
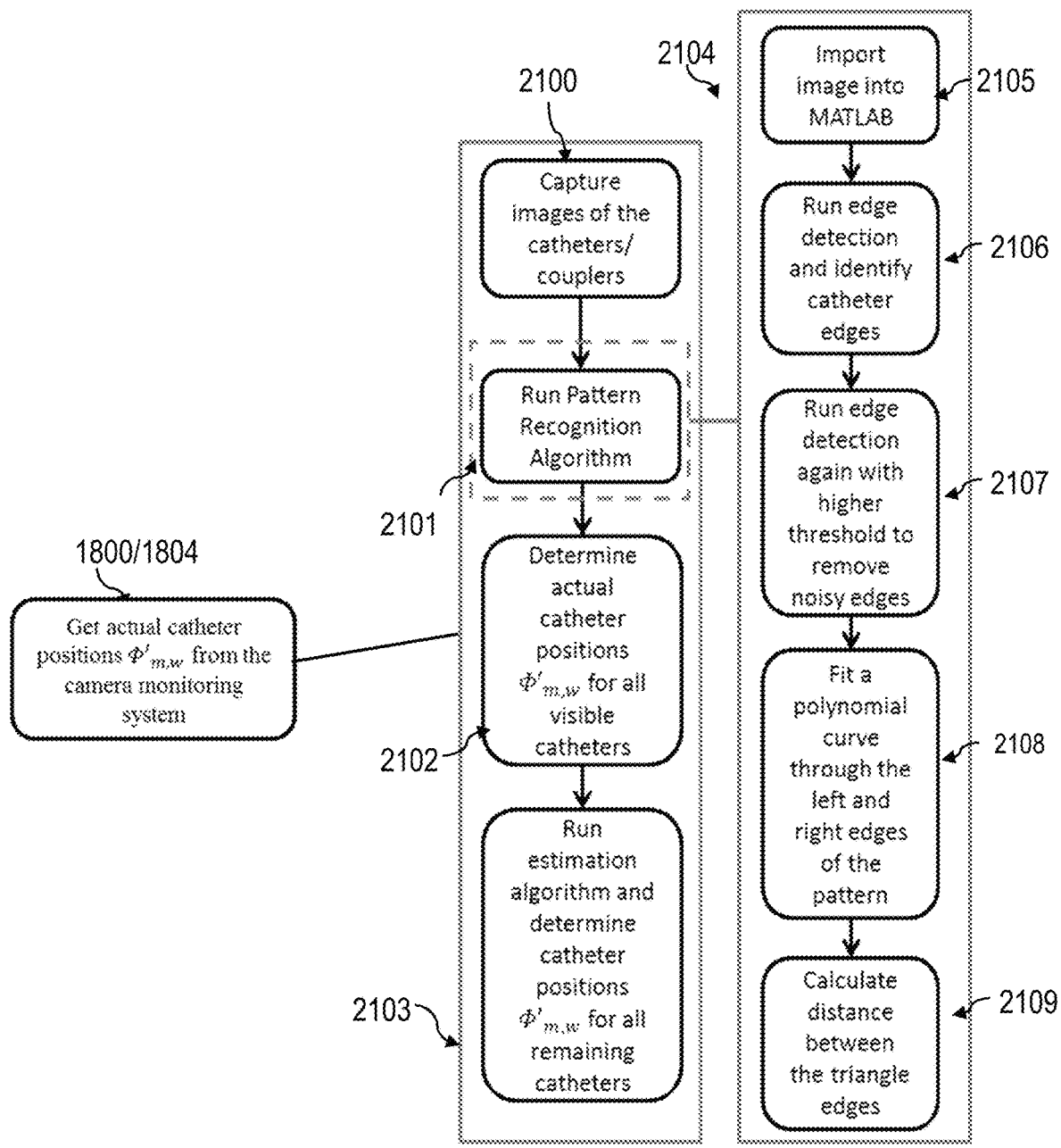
FIG. 21 is a catheter position monitoring and control process flow, according to an aspect of the present invention.

The entire monitoring and control process is depicted in FIG. 21. The left hand portion of the drawing shows the process 1800 from FIG. 18. The actual catheter position is determined by the process on the right hand side. In step 2100, the sensors 1601a-j capture images of the catheters/couplers. In step 2101, a pattern recognition algorithm 2104 is run on the images. The pattern recognition algorithm 2104 consists of the following steps. First, the image is imported into MATLAB (step 2105). Edge detection is run on the image to identify catheter edges (step 2106). Then, edge detection is run again with a higher threshold to remove noisy edges (step 2107). A polynomial curve is then fit through the left and right edges of the pattern (step 2108). The distance between the triangle edges is calculated after the curve-fits are acquired (step 2109). Once the pattern recognition algorithm of step 2101 completed, the actual catheter positions are determined for all visible catheters in step 2102. In step 2103, an estimation algorithm is run to determine catheter positions for all remaining catheters.

The following parameters were used for the example obtained from the system.

$$\text{Resolution } r = 0.027 \frac{\text{mm}}{\text{pixel}} \qquad \text{(Eq. 20)}$$

Triangle base length $b = 14$ mm

True catheter position $\Phi_{m,w} = 229.5°$

Figure 22A:
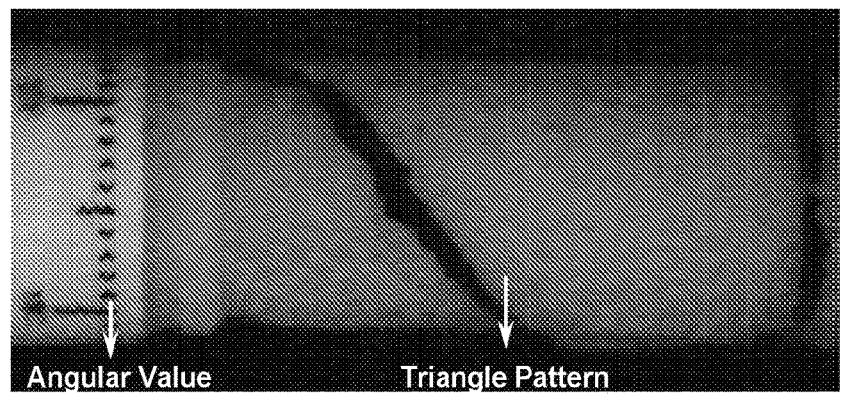
FIGS. 22a-c and 23a-f show captured images of components of the RSBT system according to aspects of the present invention.
Figure 22B:
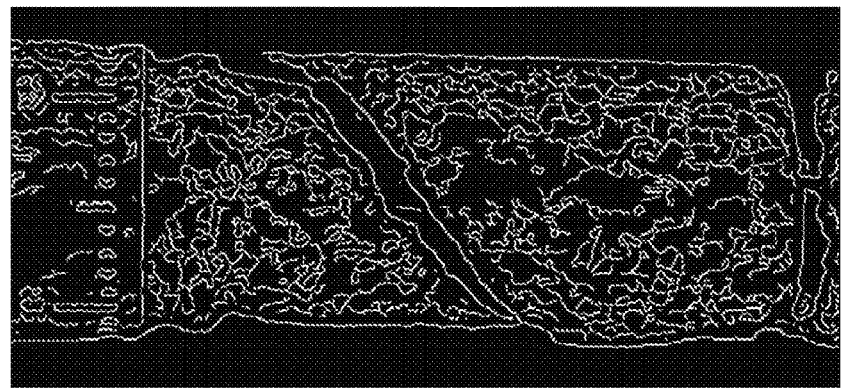
Figure 22C:
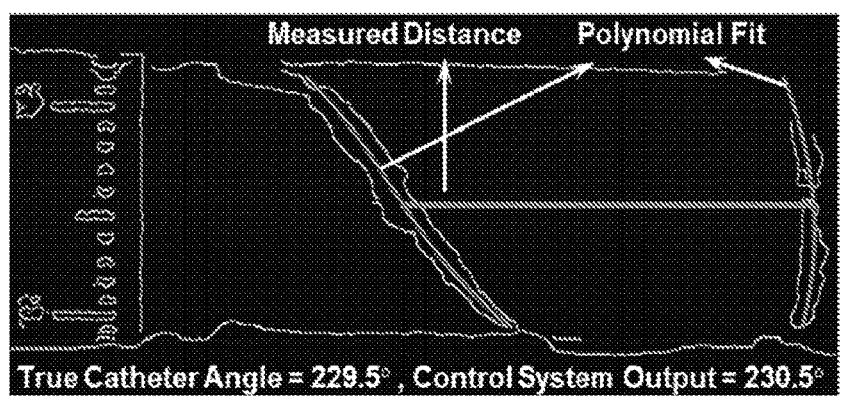
Figure 23A:
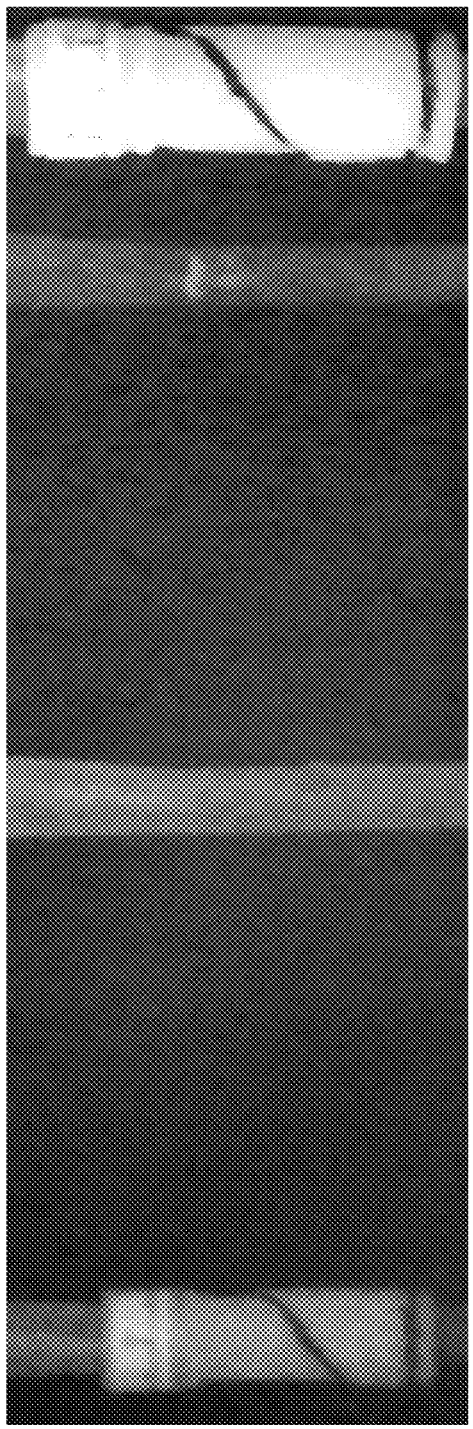
Figure 23B:
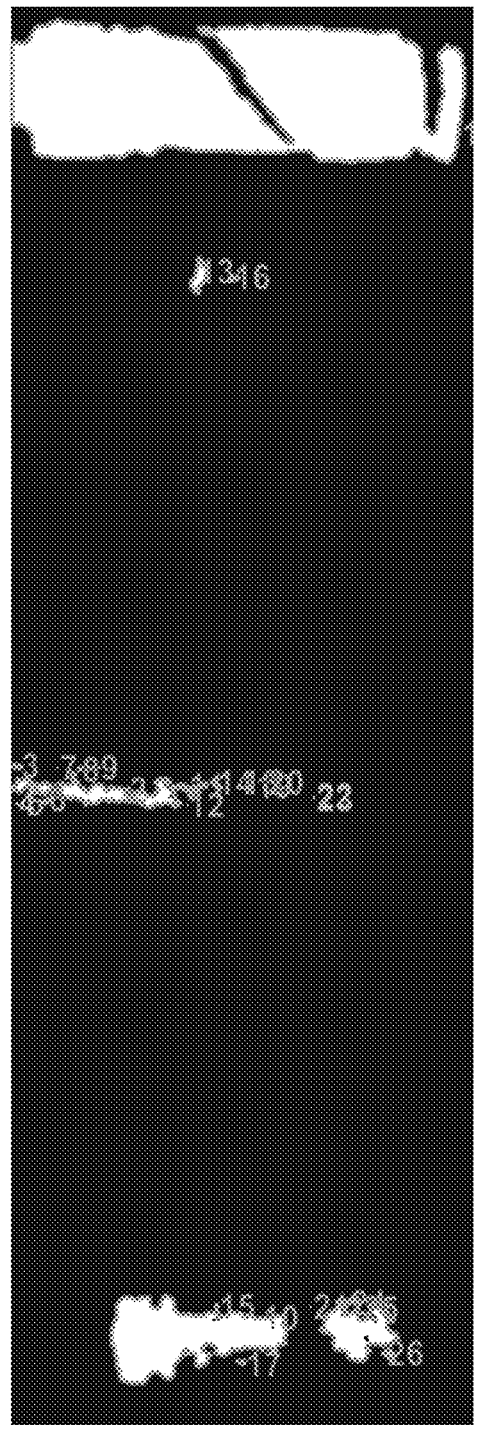
Figure 23D:
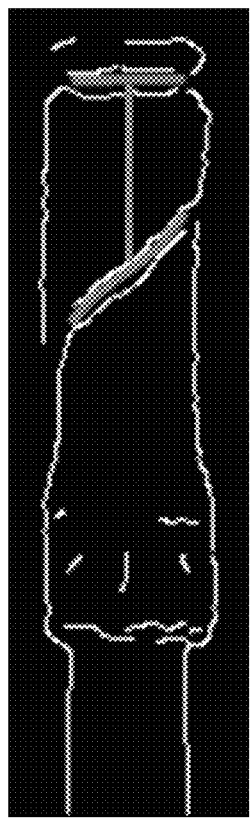
Figure 23F:
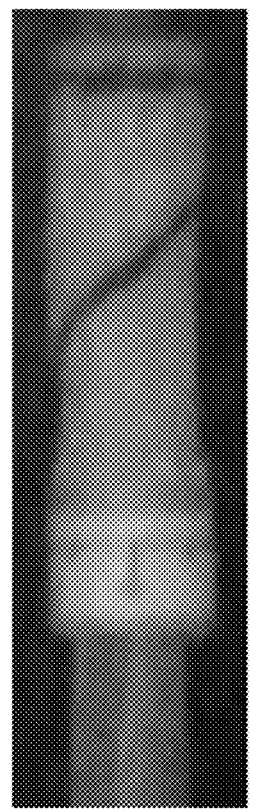
Figure 23C:
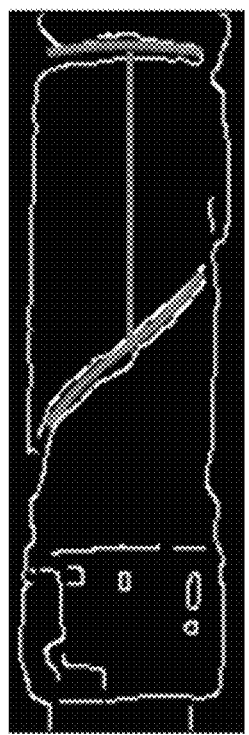
Figure 23E:
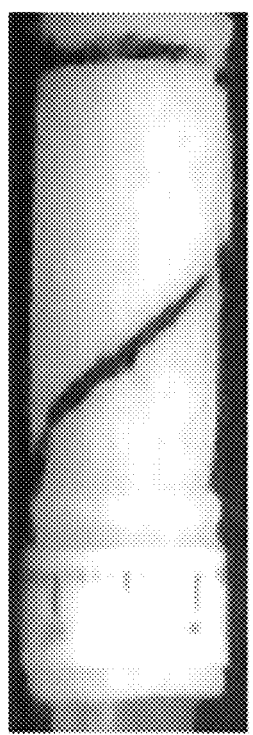

The results from the pattern recognition software are shown in FIG. 22. FIG. 22a shows the image captured by the camera with the angular ruler on the left and the triangle pattern on right. ImageJ software was used to determine the true catheter angle based on the center of the catheter. Canny edge detection results for a lower threshold are shown in FIG. 22b where the catheter boundary can be clearly seen and used to identify the center of the catheter. The noisy edges can also be seen due to the lower threshold. FIG. 22c shows the final output from the polynomial curve fit and the pixel distance measured along the center of the catheter. The output from the control system was:

$$\text{Actual catheter position } \Phi'_{m,w} = 230.5° \qquad \text{(Eq. 21)}$$

The achievable angular accuracy of ±1.5° obtained from the simulation was confirmed using an embodiment of the system.

Integration of Monitoring and Control System with a Multi-Catheter Setup

The pattern recognition algorithm was extended to a multi-catheter setup. After the catheter image captured by the camera was imported into Matlab, a boundary detection algorithm was used to detect object boundaries and identify the number of catheters in the image. The image was then divided into sub-images based on the catheter boundary and the number of catheters detected in the image. The pattern recognition algorithm for a single catheter (steps 2106-2109) was then applied to the sub-images to determine the angle of rotation of each catheter.

The results from the pattern recognition software for the multi-catheter setup are shown in FIG. 23. FIG. 23a shows the image of the two catheters. ImageJ software was used to determine the true catheter angle based on the respective catheter centers. Object boundary detection results for the image are shown in FIG. 23b based on which the number of catheters is determined. FIGS. 23c and 23e show the sub-images obtained from the original image that depict the individual catheters. FIGS. 23d and 23f show Canny edge detection results and final output from the polynomial curve fit with the fit lines and the pixel distance measured along the center of the catheter.

The true catheter angles and the output from the control system are:

True catheter position $\Phi\_1 = 229.5°$

Actual catheter position $\llbracket \varphi \rrbracket\_1 = 228.3°$

True catheter position $\Phi\_2 = 169.4°$

Actual catheter position $\llbracket \varphi \rrbracket\_2 = 172.1°$ (Eq. 22)

An angular accuracy of ±3.0° was achieved for the multi-catheter setup using an embodiment of the system.

Figure 8:
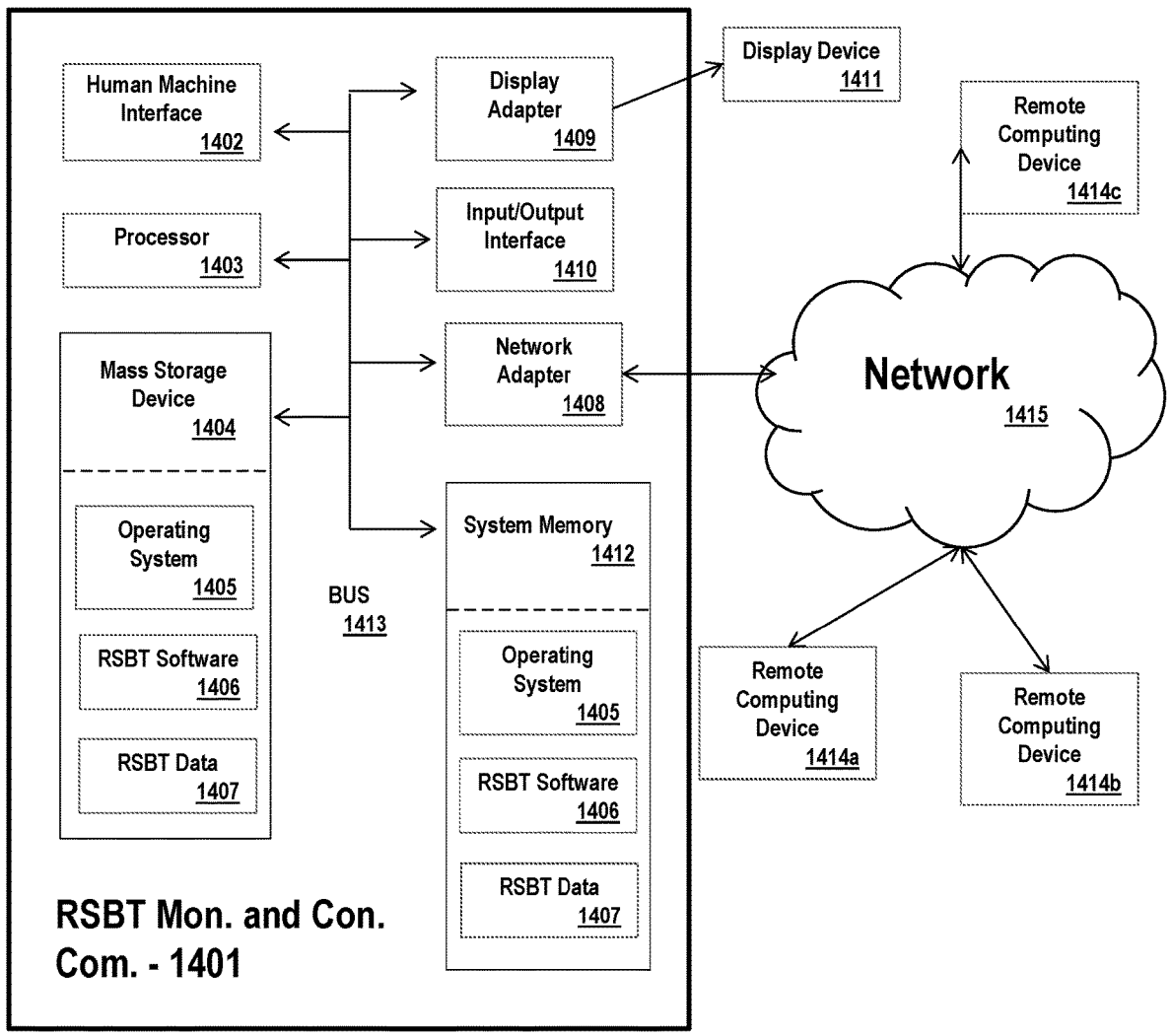
FIG. 8 is a block diagram of a computer according to an aspect of the present invention.

FIG. 8 is a block diagram illustrating an exemplary operating environment for performing a portion of disclosed methods according to an embodiment of the present invention. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

Further, one skilled in the art will appreciate that the systems and methods disclosed herein can utilize a specialized computing device in the form of a RSBT monitoring and controlling computer 1401. The methods discussed above can be performed by the computer 1401. For example, the RSBT monitoring and controlling computer 1401 can perform the duties and responsibilities of the controller discussed above.

The components of the RSBT monitoring and controlling computer 1401 can comprise, but are not limited to, one or more processors or processing units 1403, a system memory 1412, and a system bus 1413 that couples various system components including the processor 1403 to the system memory 1412. In the case of multiple processing units 1403, the system can utilize parallel computing.

The system bus 1413 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 1413, and all buses specified in this description can also be implemented over a wired or wireless network connection and each of the subsystems, including the processor 1403, a mass storage device 1404, an operating system 1405, RSBT software 1406, data 1407, a network adapter 1408, system memory 1412, an Input/Output Interface 1410, a display adapter 1409, a display device 1411, and a human machine interface 1402, can be contained within one or more remote computing devices 1414a,b,c at physically separate locations, connected through buses of this form, in effect implementing a fully distributed system.

The RSBT monitoring and controlling computer 1401 typically comprises a variety of computer readable media. Exemplary readable media can be any available media that is accessible by the RSBT monitoring and controlling computer 1401 and comprises, for example and not meant to be limiting, both volatile and non-volatile media, removable and non-removable media. The system memory 1412 comprises computer readable media in the form of volatile memory, such as random access memory (RAM), and/or non-volatile memory, such as read only memory (ROM). The system memory 1412 typically contains data such as data 1407 and/or program modules such as operating system 1405 and RSBT software 1406 (i.e., controlling the various controllers, motors, etc., discussed above) that are immediately accessible to and/or are presently operated on by the processing unit 1403.

In another aspect, the RSBT monitoring and controlling computer 1401 can also comprise other removable/non-removable, volatile/non-volatile computer storage media. By way of example, FIG. 8 illustrates a mass storage device 1404, which can provide non-volatile storage of computer code, computer readable instructions, data structures, program modules, and other data for the RSBT monitoring and controlling computer 1401. For example and not meant to be limiting, a mass storage device 1404 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 1404, including by way of example, an operating system 1405 and RSBT software 1406. Each of the operating system 1405 and RSBT software 1406 (or some combination thereof) can comprise elements of the programming and the RSBT software 1406. Data 1407 can also be stored on the mass storage device 1404. Data 1407 can be stored in any of one or more databases known in the art. Examples of such databases include DB2®, Microsoft® Access, Microsoft® SQL Server, Oracle®, mySQL, PostgreSQL, and the like. The databases can be centralized or distributed across multiple systems.

In another aspect, the user can enter commands and information into the RSBT monitoring and controlling computer 1401 via an input device (not shown). Examples of such input devices comprise, but are not limited to, a keyboard, pointing device (e.g., a "mouse"), a microphone, a joystick, a scanner, tactile input devices such as gloves, and other body coverings, and the like. These and other input devices can be connected to the processing unit 1403 via a human machine interface 1402 that is coupled to the system bus 1413, but can be connected by other interface and bus structures, such as a parallel port, game port, an IEEE 1394 Port (also known as a Firewire port), a serial port, or a universal serial bus (USB).

In yet another aspect, a display device 1411 can also be connected to the system bus 1413 via an interface, such as a display adapter 1409. It is contemplated that the RSBT monitoring and controlling computer 1401 can have more than one display adapter 1409 and more than one display device 1411. For example, a display device can be a monitor, an LCD (Liquid Crystal Display), or a projector. In addition to the display device 1411, other output peripheral devices can comprise components such as speakers (not shown) and a printer (not shown) which can be connected to the computer 1401 via Input/Output Interface 1410. Any step and/or result of the methods can be output in any form to an output device. Such output can be any form of visual representation, including, but not limited to, textual, graphical, animation, audio, tactile, and the like.

The RSBT monitoring and controlling computer 1401 can operate in a networked environment using logical connections to one or more remote computing devices 1414a,b,c. By way of example, a remote computing device can be a personal computer, a laptop computer, portable computer, a server, a router, a network computer, a peer device or other common network node, and so on. Logical connections between the RSBT monitoring and controlling computer 1401 and a remote computing device 1414a,b,c can be made via a local area network (LAN) and a general wide area network (WAN). Such network connections can be through a network adapter 1408. A network adapter 1408 can be implemented in both wired and wireless environments. Such networking environments are conventional and commonplace in offices, enterprise-wide computer networks, intranets, and the Internet 1415.

According to an aspect, the RSBT monitoring and controlling computer 1401, via the RSBT software 1406, can control the operation of the RSBT system.

For purposes of illustration, application programs and other executable program components such as the operating system 1405 are illustrated herein as discrete blocks, although it is recognized that such programs and components reside at various times in different storage components of the RSBT monitoring and controlling computer 1401, and are executed by the data processor(s) of the computer. An implementation of RSBT software 1406 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The system and methods disclosed above are predicted to have a major impact on cancer treatment, specifically in cases of prostate cancer. Ultimately, it is thought that the RSBT system and methods discussed above will lead to a prostate cancer intervention that will provide clinicians with the unprecedented capability to reduce radiation dose to the urethra by 20-40%, rectum by 5-7%, and bladder by 5-7%, without reducing prostate dose relative to conventional systems. It has been demonstrated that reducing urethral dose reduces toxicity, and it has been shown that reducing the HDR-BT dose per fraction from 9.5 Gy per treatment fraction (2 fractions delivered) to 6 Gy per fraction (3 fractions delivered)—a 37% dose-per-fraction reduction—reduced grade ≥2 urethral stricture rates by 28.2 percentage points (31.6% vs. 3.4%). Thus RSBT provides the benefits of high-dose prostate treatments without the increased toxicity.

In an aspect, the RSBT delivery system described above has several other advantages. First, the translational and rotational motion control methods are de-coupled, enabling rapid source insertion and removal into the interstitial needles implanted in the patient. This is particularly important in the case where emergency source retraction is necessary. In addition, radiation sources are stored in the afterloader device, making them straightforward to change after their activity has decayed enough to require replacement approximately every half-life (2800 days for $^{153}$Gd). Further, the partially-shielded radiation sources in all needles (20, for example) placed in the prostate can be rotated simultaneously. Likewise, the angular orientations of all radiation source shields are always known by the user, as all sources are pointed in the same direction at any given time. Along the same lines, the needles that are inserted into the patient are maintained in the same orientation throughout the treatment, and the catheters are moved inside the needles, controlling the source position and shield orientation. With this technique, tissue is not disturbed during the delivery process. And lastly, the delivery method provides the flexibility to enable intelligent positioning of radiation sources throughout the treatment, minimizing inter-source interference. This is accomplished by controlling the translational positions of the sources in a manner such that they avoid each other.

It is expected that the improvement in the delivered radiation dose distributions will reduce the probability of prostate cancer patients experiencing treatment-related side effects, improving quality of life. In addition RSBT systems and methods discussed above could be used to escalate prostate cancer dose without increasing dose to healthy tissues beyond conventional methods, which could improve metastasis-free tumor control in the long term, at 10+ years post-treatment.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention. To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, those skilled in the art will appreciate that the within disclosures are exemplary only and that various other alternatives, adaptations, and modifications may be made within the scope of the present invention. Accordingly, the present invention is not limited to the specific embodiments as illustrated herein, but is only limited by the following claims.

REFERENCES

1. R. L. Siegel, K. D. Miller and A. Jemal, "Cancer statistics, 2015," CA Cancer J Clin 65, 5-29 (2015).

2. SEER, "Surveillance, Epidemiology, and End Results (SEER) Program (www.seer.cancer.gov) SEER*Stat Database version 7.0.4: Incidence—SEER 9 Regs Research Data, November 2010 Sub (2004-2008)—Linked to County Attributes—Total U.S., 1969-2009 Counties, National Cancer Institute, DCCPS, Surveillance Research Program, Cancer Statistics Branch, released April 2011, based on the November 2010 submission.," (2011).
3. R. C. Chen, J. A. Clark and J. A. Talcott, "Individualizing quality-of-life outcomes reporting: how localized prostate cancer treatments affect patients with different levels of baseline urinary, bowel, and sexual function," J Clin Oncol 27, 3916-3922 (2009).
4. M. J. Zelefsky, Z. Fuks, M. Hunt, Y. Yamada, C. Marion, C. C. Ling, H. Amols, E. S. Venkatraman and S. A. Leibel, "High-dose intensity modulated radiation therapy for prostate cancer: early toxicity and biochemical outcome in 772 patients," Int J Radiat Oncol 53, 1111-1116 (2002).
5. P. D. Grimm, J. C. Blasko, J. E. Sylvester, R. M. Meier and W. Cavanagh, "10-year biochemical (prostate-specific antigen) control of prostate cancer with (125)I brachytherapy," Int J Radiat Oncol Biol Phys 51, 31-40 (2001).
6. Y. Yoshioka, T. Nose, K. Yoshida, R. J. Oh, Y. Yamada, E. Tanaka, H. Yamazaki and T. Inoue, "High-dose-rate brachytherapy as monotherapy for localized prostate cancer: a retrospective analysis with special focus on tolerance and chronic toxicity," Int J Radiat Oncol Biol Phys 56, 213-220 (2003).
7. J. E. Sylvester, P. D. Grimm, J. C. Blasko, J. Millar, P. F. Orio, 3rd, S. Skoglund, R. W. Galbreath and G. Merrick, "15-Year biochemical relapse free survival in clinical Stage T1-T3 prostate cancer following combined external beam radiotherapy and brachytherapy; Seattle experience," Int J Radiat Oncol Biol Phys 67, 57-64 (2007).
8. P. Grimm, I. Billiet, D. Bostwick, A. P. Dicker, S. Frank, J. Immerzeel, M. Keyes, P. Kupelian, W. R. Lee, S. Machtens, J. Mayadev, B. J. Moran, G. Merrick, J. Millar, M. Roach, R. Stock, K. Shinohara, M. Scholz, E. Weber, A. Zietman, M. Zelefsky, J. Wong, S. Wentworth, R. Vera and S. Langley, "Comparative analysis of prostate-specific antigen free survival outcomes for patients with low, intermediate and high risk prostate cancer treatment by radical therapy. Results from the Prostate Cancer Results Study Group," BJU international 109 Suppl 1, 22-29 (2012).
9. M. G. Sanda, R. L. Dunn, J. Michalski, H. M. Sandler, L. Northouse, L. Hembroff, X. Lin, T. K. Greenfield, M. S. Litwin, C. S. Saigal, A. Mahadevan, E. Klein, A. Kibel, L. L. Pisters, D. Kuban, I. Kaplan, D. Wood, J. Ciezki, N. Shah and J. T. Wei, "Quality of life and satisfaction with outcome among prostate-cancer survivors," N Engl J Med 358, 1250-1261 (2008).
10. M. R. Cooperberg, N. R. Ramakrishna, S. B. Duff, K. E. Hughes, S. Sadownik, J. A. Smith and A. K. Tewari, "Primary treatments for clinically localised prostate cancer: a comprehensive lifetime cost-utility analysis," BJU international 111, 437-450 (2013).
11. H. Zhang, E. M. Messing, L. B. Travis, O. Hyrien, R. Chen, M. T. Milano and Y. Chen, "Age and Racial Differences among PSA-Detected (AJCC Stage T1cN0M0) Prostate Cancer in the U.S.: A Population-Based Study of 70,345 Men," Frontiers in oncology 3, 312 (2013).
12. Active surveillance for prostate cancer: What a man needs to know before deciding on treatment, Mar. 9, 2014, http://urology.jbu.edu/prostate/advice1.php.
13. A. A. Martinez, J. Gonzalez, H. Ye, M. Ghilezan, S. Shetty, K. Kernen, G. Gustafson, D. Krauss, F. Vicini and L. Kestin, "Dose escalation improves cancer-related events at 10 years for intermediate- and high-risk prostate cancer patients treated with hypofractionated high-dose-rate boost and external beam radiotherapy," Int J Radiat Oncol 79, 363-370 (2011).
14. J. B. Malcolm, M. D. Fabrizio, B. B. Barone, R. W. Given, R. S. Lance, D. F. Lynch, J. W. Davis, M. E. Shaves and P. F. Schellhammer, "Quality of life after open or robotic prostatectomy, cryoablation or brachytherapy for localized prostate cancer," J Urol 183, 1822-1828 (2010).
15. J. W. Robinson, S. Moritz and T. Fung, "Meta-analysis of rates of erectile function after treatment of localized prostate carcinoma," Int J Radiat Oncol Biol Phys 54, 1063-1068 (2002).
16. N. Mohammed, L. Kestin, M. Ghilezan, D. Krauss, F. Vicini, D. Brabbins, G. Gustafson, H. Ye and A. Martinez, "Comparison of acute and late toxicities for three modern high-dose radiation treatment techniques for localized prostate cancer," Int J Radiat Oncol 82, 204-212 (2012).
17. B. R. Hindson, J. L. Millar and B. Matheson, "Urethral strictures following high-dose-rate brachytherapy for prostate cancer: analysis of risk factors," Brachytherapy 12, 50-55 (2013).
18. A. C. Pellizzon, W. Nadalin, J. V. Salvajoli, R. C. Fogaroli, P. E. Novaes, M. A. Maia and R. Ferrigno, "Results of high dose rate afterloading brachytherapy boost to conventional external beam radiation therapy for initial and locally advanced prostate cancer," Radiotherapy and Oncology 66, 167-172 (2003).
19. L. Sullivan, S. G. Williams, K. H. Tai, F. Foroudi, L. Cleeve and G. M. Duchesne, "Urethral stricture following high dose rate brachytherapy for prostate cancer," Radiother Oncol 91, 232-236 (2009).
20. D. J. Demanes, R. R. Rodriguez, L. Schour, D. Brandt and G. Altieri, "High-dose-rate intensity-modulated brachytherapy with external beam radiotherapy for prostate cancer: California endocurietherapy's 10-year results," Int J Radiat Oncol Biol Phys 61, 1306-1316 (2005).
21. L. Astrom, D. Pedersen, C. Mercke, S. Holmang and K. A. Johansson, "Long-term outcome of high dose rate brachytherapy in radiotherapy of localised prostate cancer," Radiother Oncol 74, 157-161 (2005).
22. P. Hoskin, A. Rojas, G. Lowe, L. Bryant, P. Ostler, R. Hughes, J. Milner and H. Cladd, "High-dose-rate brachytherapy alone for localized prostate cancer in patients at moderate or high risk of biochemical recurrence," Int J Radiat Oncol 82, 1376-1384 (2012).
23. M. J. Zelefsky, S. A. Leibel, P. B. Gaudin, G. J. Kutcher, N. E. Fleshner, E. S. Venkatramen, V. E. Reuter, W. R. Fair, C. C. Ling and Z. Fuks, "Dose escalation with three-dimensional conformal radiation therapy affects the outcome in prostate cancer," Int J Radiat Oncol Biol Phys 41, 491-500 (1998).
24. Q. E. Adams, J. Xu, E. K. Breitbach, X. Li, S. A. Enger, W. R. Rockey, Y. Kim, X. Wu and R. T. Flynn, "Interstitial rotating shield brachytherapy for prostate cancer," Med Phys 41, 051703 (2014).
25. T. Akimoto, K. Ito, J. Saitoh, S. E. Noda, K. Harashima, H. Sakurai, Y. Nakayama, T. Yamamoto, K. Suzuki, T. Nakano and H. Niibe, "Acute genitourinary toxicity after 25. high-dose-rate (HDR) brachytherapy combined with hypofractionated external-beam radiation therapy for localized prostate cancer: correlation between the urethral dose in HDR brachytherapy and the severity of acute genitourinary toxicity," Int J Radiat Oncol Biol Phys 63, 463-471 (2005).
26. T. Akimoto, H. Katoh, Y. Kitamoto, K. Shirai, M. Shioya and T. Nakano, "Anatomy-based inverse optimization in high-dose-rate brachytherapy combined with hypofractionated external beam radiotherapy for localized prostate cancer: comparison of incidence of acute genitourinary toxicity between anatomy-based inverse optimization and geometric optimization," Int J Radiat Oncol Biol Phys 64, 1360-1366 (2006).
27. T. Akimoto, H. Katoh, S. E. Noda, K. Ito, T. Yamamoto, B. Kashiwagi and T. Nakano, "Acute genitourinary toxicity after high dose rate (HDR) brachytherapy combined with hypofractionated external-beam radiation therapy for localized prostate cancer: Second analysis to determine the correlation between the urethral dose in HDR brachytherapy and the severity of acute genitourinary toxicity," Int J Radiat Oncol Biol Phys 63, 472-478 (2005).
28. G. C. Morton, D. A. Loblaw, H. Chung, G. Tsang, R. Sankreacha, A. Deabreu, L. Zhang, A. Mamedov, P. Cheung, D. Batchelar, C. Danjoux and E. Szumacher, "Health-related quality of life after single-fraction high-dose-rate brachytherapy and hypofractionated external beam radiotherapy for prostate cancer," Int J Radiat Oncol Biol Phys 80, 1299-1305 (2011).
29. H. Ishiyama, M. Kitano, T. Satoh, S. Kotani, M. Uemae, K. Matsumoto, H. Okusa, K. Tabata, S. Baba and K. Hayakawa, "Genitourinary toxicity after high-dose-rate (HDR) brachytherapy combined with Hypofractionated External beam radiotherapy for localized prostate cancer: an analysis to determine the correlation between dose-volume histogram parameters in HDR brachytherapy and severity of toxicity," Int J Radiat Oncol 75, 23-28 (2009).
30. I. C. Hsu, K. Bae, K. Shinohara, J. Pouliot, J. Purdy, G. Ibbott, J. Speight, E. Vigneault, R. Ivker and H. Sandler, "Phase II trial of combined high-dose-rate brachytherapy and external beam radiotherapy for adenocarcinoma of the prostate: preliminary results of RTOG 0321," Int J Radiat Oncol Biol Phys 78, 751-758 (2010).
31. I. C. Hsu, D. Hunt, W. Straube, J. Pouliot, A. Cunha, D. Krishnamurthy and H. Sandler, "Dosimetric analysis of radiation therapy oncology group 0321: The importance of urethral dose," Practical Radiation Oncology 4, 27-34 (2014).
32. R. Potter, P. Georg, J. C. Dimopoulos, M. Grimm, D. Berger, N. Nesvacil, D. Georg, M. P. Schmid, A. Reinthaller, A. Sturdza and C. Kirisits, "Clinical outcome of protocol based image (MRI) guided adaptive brachytherapy combined with 3D conformal radiotherapy with or without chemotherapy in patients with locally advanced cervical cancer," Radiother Oncol 100, 116-123 (2011).
33. W. Yang, Y. Kim, X. Wu, Q. Song, Y. Liu, S. K. Bhatia, W. Sun and R. T. Flynn, "Rotating-shield brachytherapy for cervical cancer," Phys Med Biol 58, 3931-3941 (2013).
34. Y. Liu, R. T. Flynn, W. Yang, Y. Kim, S. K. Bhatia, W. Sun and X. Wu, "Rapid emission angle selection for rotating-shield brachytherapy," Med Phys 40, 051720 (2013).
35. S. A. Enger, D. R. Fisher and R. T. Flynn, "Gadolinium-153 as a brachytherapy isotope," Phys Med Biol 58, 957-964 (2013).
36. Y. Yamada, L. Rogers, D. J. Demanes, G. Morton, B. R. Prestidge, J. Pouliot, G. N. Cohen, M. Zaider, M. Ghilezan and I. C. Hsu, "American Brachytherapy Society consensus guidelines for high-dose-rate prostate brachytherapy," Brachytherapy 11, 20-32 (2012).
37. B. Julius, S. Lin, D. Rahmani, W. Rockey, C. Tracy, E. Nixon, J. M. Modrick, E. Sander and Y. Kim, "Development of a low cost, easily-made, interchangeable, prostate brachytherapy phantom for multi-imaging guidance using ultrasound, CT, and MRI," Med. Phys. 40, 157 (2013).
38. M. Schmid, J. M. Crook, D. Batchelar, C. Araujo, D. Petrik, D. Kim and R. Halperin, "A phantom study to assess accuracy of needle identification in real-time planning of ultrasound-guided high-dose-rate prostate implants," Brachytherapy 12, 56-64 (2013).
39. Y. Kim, M. Muruganandham, J. M. Modrick and J. E. Bayouth, "Evaluation of artifacts and distortions of titanium applicators on 3.0-Tesla MRI: feasibility of titanium applicators in MRI-guided brachytherapy for gynecological cancer," Int J Radiat Oncol Biol Phys 80, 947-955 (2011).
40. X. Li, Q. Adams and R. Flynn, "Dosimetric Validation of a Partially-Shielded Gd-153 Brachytherapy Concept," Med. Phys. 41, 91 (2014).
41. E. C. White, M. R. Kamrava, J. Demarco, S. J. Park, P. C. Wang, O. Kayode, M. L. Steinberg and D. J. Demanes, "High-Dose-Rate Prostate Brachytherapy Consistently Results in High Quality Dosimetry," Int J Radiat Oncol Biol Phys 85, 543-548 (2012).
42. M. A. Ebert, "Possibilities for intensity-modulated brachytherapy: technical limitations on the use of non-isotropic sources," Phys Med Biol 47, 2495-2509 (2002).
43. M. A. Ebert, "Potential dose-conformity advantages with multi-source intensity-modulated brachytherapy (IMBT)," Australas Phys Eng Sci Med 29, 165-171 (2006).
44. L. Lin, R. R. Patel, B. R. Thomadsen and D. L. Henderson, "The use of directional interstitial sources to improve dosimetry in breast brachytherapy," Med Phys 35, 240-247 (2008).
45. C. Shi, B. Guo, C. Y. Cheng, C. Esquivel, T. Eng and N. Papanikolaou, "Three dimensional intensity modulated brachytherapy (IMBT): dosimetry algorithm and inverse treatment planning," Med Phys 37, 3725-3737 (2010).
46. W. Yang, Y. Kim, X. Wu, Q. Song, Y. Liu, S. K. Bhatia, W. Sun and R. T. Flynn, "Rotating-shield brachytherapy for cervical cancer," Phys Med Biol 58, 3931-3941 (2013).
47. Y. Liu, R. T. Flynn, W. Yang, Y. Kim, S. K. Bhatia, W. Sun and X. Wu, "Rapid emission angle selection for rotating-shield brachytherapy," Med Phys 40, 051720 (2013).
48. Y. Liu, R. T. Flynn, Y. Kim, W. Yang and X. Wu, "Dynamic rotating-shield brachytherapy," Med Phys 40, 121703 (2013).
49. Q. E. Adams, J. Xu, E. K. Breitbach, X. Li, S. A. Enger, W. R. Rockey, Y. Kim, X. Wu and R. T. Flynn, "Interstitial rotating shield brachytherapy for prostate cancer," Med Phys 41, 051703 (2014).

U.S. Pat. No. 6,066,083
U.S. Pat. No. 6,741,631
U.S. Pat. No. 6,482,142
U.S. Pat. No. 6,796,936
U.S. Pat. No. 7,407,476

U.S. Pat. No. 7,556,596
U.S. Pat. No. 7,651,458
U.S. Pat. No. 7,686,755
U.S. Pat. No. 7,762,940
US 2008/0043903
US 2007/0167667 A1
US 2007/0191667 A1
US 2008/0004478
US 2008/0146861 A1
US 2009/0216062
US 2010/0036190 A1
U.S. Pat. No. 6,527,693
US 2005/0113629
US 2010/0222628
US 2012/0157748
US 2009/0246126
US 2004/0254418

What is claimed is:

1. A rotating shield brachytherapy (RSBT) system comprising:
   a. a plurality of RSBT delivery devices, each RSBT delivery device comprising:
      i. a catheter comprising a radiation source, a shield, and an emissions window;
   b. a plurality of needles configured to be placed within a subject, each of the needles configured to receive a portion of at least one of the plurality of RSBT delivery devices;
   c. a delivery system configured to:
      i. rotate the plurality of RSBT delivery devices to a given emissions window angle; and
      ii. for the given emissions window angle applied to all RSBT delivery devices, translate the plurality of RSBT delivery devices independently from one another with the given emissions window angle to adjust a depth of each RSBT delivery device, and therefore a depth of the given emission windows of each RSBT delivery device independent from each other; and
   d. a catheter position verification and correction system configured to verify positions of the plurality of catheters during and before a RSBT session.

2. The RSBT system of claim 1, wherein the delivery system comprises:
   a plurality of rotating shafts, wherein each of the plurality of rotating shafts is configured to be coupled to one of the plurality of RSBT delivery devices;
   a first fixed template;
   a second fixed template;
   a moving template between the first fixed template and the second fixed template, wherein each of the templates comprises a plurality of apertures configured to receive and guide the plurality of rotating shafts; and
   at least one motor to translate the moving template between the first and second fixed templates, wherein the translation of the moving template rotates the plurality of rotating shafts, which rotates the plurality of RSBT delivery devices, including the plurality of the catheters and the emission windows, to selected angles.

3. The RSBT system of claim 1; wherein the catheter position verification and correction system comprises at least one sensor configured to determine the rotation of the plurality of catheters.

4. The RSBT system of claim 3, wherein the at least one sensor comprises a camera configured to capture and monitor an angle-dependent pattern on each of the plurality of catheters.

5. The RSBT system of claim 4, wherein the camera comprises a plurality of cameras.

6. The RSBT system of claim 5, wherein the plurality of cameras are oriented such that each catheter is visible from at least two cameras.

7. The RBST system of claim 2; wherein each of the plurality of rotating shafts comprises a helical key configured to engage and interact with the plurality of apertures of the moving template.

8. The RSBT system of claim 7, further comprising a plurality of connectors, each connector configured to translate motion from the rotating shafts to the catheters.

9. The RSBT system of claim 8, wherein each of the plurality of catheters further comprises a keyed cuff configured to engage with each of the plurality of connector.

10. The RSBT system of claim 2, further comprising a plurality of linear actuators configured to move linearly the catheters within the needles.

* * * * *